(12) United States Patent
Schechter et al.

(10) Patent No.: US 6,638,508 B2
(45) Date of Patent: Oct. 28, 2003

(54) MODIFIED AVIDIN-TYPE MOLECULES AS TARGETING AGENTS FOR THE LIVER AND CELLS OF THE RETICULOENDOTHELIAL SYSTEM

(75) Inventors: Bilha Schechter, Rehovot (IL); Ruth Arnon, Rehovot (IL); Meir Wilchek, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/100,015

(22) Filed: Jun. 19, 1998

(65) Prior Publication Data

US 2002/0009416 A1 Jan. 24, 2002

Related U.S. Application Data

(63) Continuation of application No. PCT/US96/20333, filed on Dec. 20, 1996.

(30) Foreign Application Priority Data

Dec. 21, 1995 (IL) ................................................. 116500

(51) Int. Cl.[7] ...................... A61K 39/395; A61K 49/00; A61K 38/02; A61K 51/00; A61K 47/42
(52) U.S. Cl. ...................... 424/157.1; 424/9; 424/1.69; 514/2
(58) Field of Search ...................... 424/9, 134.1, 152.1, 424/157.1, 1.69; 514/2

(56) References Cited

U.S. PATENT DOCUMENTS

| | | |
|---|---|---|
| 5,534,499 A | 7/1996 | Ansell |
| 5,644,049 A | 7/1997 | Giusti et al. |
| 6,046,177 A | 4/2000 | Stella et al. |

OTHER PUBLICATIONS

Del Rosario et al. Cancer Res. (Suppl.) 50:8045–8085, 1990.*

Pimm et al., Gamma scintigraphy of the biodistribution of [123]I–labelled N–(2–hydroxypropyl) methacrylamide copolymer–doxorubicin conjugates in mice with transplanted melanoma and mammary carcinoma, *Journal of Drug Targeting*, 3:375–383 (1996).

Duncan et al., The role of polymer conjugates in the diagnosis and treatment of cancer, *S.T.P. Pharma Sciences*, 6(4)237–263 (1996).

Aboud–Pirak et al., "Inhibition of human tumor growth in nude mice by a conjugate of doxorubicin with monoclonal antibodies to epidermal growth factor receptor", *Proc. Natl. Acad. Sci. USA*, 68:3778–3781 (1989).

Argarana et al., "Molecular cloning and nucleotide sequence of the streptavidin gene", *Nucleic Acid Res.* 14:1871–1882, (1986).

Bayer et al. "Postsecretory modifications of streptavidin", *Biochem. J.*, 259:369–376, (1989).

Bevilacqua et al., "Endothelial Leukocyte Adhesion Molecule 1: An Inducible Receptor for Neutrophils Related Related to Complement Regulatory Proteins and Lectins", *Science*, 243:1160–1165, (1989).

Brooks et al., "Integrin Antagonists Promote Tumor Regression by Inducing Apoptosis of Angiogenic", *Cell* 79:1157–1164, (1994).

Cepek et al., "Adhesion between epithelial cells and T lymphocytes mediated by E–cadherin and the integrin", *Nature*, 372:190–193, (1994).

Chaiet et al., "The Properties of Streptavidin, a Biotin–Binding Protein Produced by Streptomycetes", *Archives of Biochemistry and Biophysics*, 106:1–5, (1964).

Ellison et al., "Limited proteolysis of native proteins: The interaction between avidin and proteinase K", *Protein Science*, 4:1337–1345, (1995).

Erbacher et al., "Glycosylated Polylysine/DNA Complexes: Gene Transfer Efficiency in Relation with the Size and the Sugar Substitution Level of Glycosylated Polylysines and with the Plasmid Size", *Bioconjugate Chem.* 6:401–410, (1995).

Fujita et al., "Control of In Vivo Fate of Albumin Derivatives Utilizing Combined Chemical Modification" *J. Drug Targeting*, 2:157–165, (1994).

Hashida et al., "Hepatic targeting of drugs and proteins by chemical modification", *J. Controlled Release* 36:99–107, (1995).

Hiller et al., "Studies on the biotin–binding site of avidin", *Biochem. J.*, 278:573–585, (1991).

Hnatowich et al., "Investigations of Avidin and Biotin for Imaging Application", *J. Nuclear Med.*, 28:1294–1302 (1987).

Hurwitz et al., "Soluble Macromolecules as Carrier for Daunorubicin", *J. Applied Biochem.*, 2:25–35, (1980).

Hurwitz et al., "The Covalent Linking of Two Nucleotide Analogues to Antibodies", *J. Medicinal Chem.*, 28:137–140, (1985).

(List continued on next page.)

*Primary Examiner*—Gary Kunz
*Assistant Examiner*—Robert C. Hayes
(74) *Attorney, Agent, or Firm*—Browdy and Neimark, PLLC

(57) ABSTRACT

The present invention relates to avidin-type molecules having 2,4,6-trinitrophenyl or lactosyl groups or being complexed with an antibody specific to the avidin-type molecule, which shifts the biodistribution pattern in tissues and organs to the liver, where these molecules accumulate at high levels over several days. These modified avidin-type molecules provide a means for delivery of diagnostic and therapeutic agents, including radionuclides to the liver and cells of the reticuloendothelial system (RES) for diagnosing and treating hepatic disorders and disorders of the RES.

38 Claims, 14 Drawing Sheets

OTHER PUBLICATIONS

Johnson et al., "Lung Endothelial Dipeptidyl Peptidase IV Is an Adhesion Molecule for Lung–metastatic Rat Breast and Prostate Carcinoma Cells", *J. Cell Biol.*, 121:1423–1432, (1993).

Johnston et al., "Cloning of GMP–140, a Granule Membrane Protein of Platelets and Endothelium: Sequence Similarity to Proteins Involved in Cell Adhesion and Inflammation", *Cell*, 56:1033–1044, (1989).

Kikutani et al., "Molecular Structure of Human Lymphocyte Receptor for Immunoglobulin E", *Cell*, 47:657–665 (1986).

Lasky et al., "Cloning of a Lymphocyte Homing Receptor Reveals a Lectin Domain", *Cells*, 56:1045–1055, (1989).

Ledley F.D., "Hepatic Gene Therapy: Present and Future", *Hepatology*, 18:1263–1273, (1993).

Ledley et al. "Development of a Clinical Protocol for Hepatic Gene Transfer: Lessons Learned in Preclinical Studies", *Pediatric Research*, 33:313–320, (1993).

Longman et al., "A two–step targeting approach for delivery of doxorubicin–loaded liposomes to tumur cells in vivo", *Cancer Chemother. Pharmacol.*, 36:91–101, (1995).

Magnusson et al., "Extremely rapid endocytosis mediated by the mannose receptor of sinusoidal endothelial rat liver cells", *Biochem. J.*, 257:651–656, (1989).

Matsumura et al., "A New Concept for Macromolecular Therapeutics in Cancer Chemotherapy: Mechanism of Tumoritropic Accumulation of Proteins and the Antitumour Agent Smancs", *Cancer Research*, 46:6387–6392, (1986).

Mulligan R.C., "The Basic Science of Gene Therapy", *Science*, 260:926–932, (1993).

Natsumeda et al., "Synergistic Cytotoxic Effect of Tiazofurin and Ribavirin in Hepatoma Cells" *Biochem. Biophys. Res. Commun.*, 153:321–327, (1988).

Neurath et al., "Blocking of CD4 Cell Receptors for the Human Immunodeficiency Virus Type 1 (HIV–1) by Chemically Modified Bovine Milk Proteins: Potential for AIDS Prophylaxis", *J. Molec. Recog.*, 8:304–316, (1995).

Ohashi et al., "Efficient transfer and sustained high expression of the human glucocerebrosidase gene in mice and their functional macrophages following transplantation of bone marrow transduced by a retroviral vector" 89:11332–11336, (1992), *Proc. Natl. Acad. Sci. USA*.

Schechter et al., "CIS–Platinum(II) Complexes of Carboxymethyl–Dextran as Potential Antitumor Agents I. Preparation and Characterization", *Cancer Biochem. Biophys.*, 8:277–288, (1986a).

Schechter et al., "CIS–Platinum (II) Complexes of Carboxymethyl–Dextran as Potential Antitumor Agents II. in Vitro and in Vivo Activity", *Cancer Biochem. Biophys.*, 8:289–298, (1986a).

Schechter et al., "Increased Therapeutic Efficacy of CIS–Platinum Complexes of Poly–L–Glutamic Acid Against a Murine Carcinoma", *Int. J. Cancer*, 39:409–413, (1987a).

Schechter et al., "Selective cytotoxicity against tumor cells by cisplatin complexed to antitumor antibodies via carboxymethyl dextran", *Cancer Immunol. Immunother*, 25:225, (1987b).

Schechter et al., "Soluble Polymers as Carriers of CIS–Platinum", *J. Controlled Release*, 10:75–87, (1989a).

Schechter et al., "Blood levels and serum protein binding of cis–Platinum(II) complex to carboxymethyl–dextran", *Cancer Chemother. Pharmacol.*, 24:161–166, (1989b).

Schechter et al., "Tissue distribution of avidin and streptavidin injected to mice", *Eur. J. Biochem.* 462:327–331, (1990).

Schechter et al., "Indirect immunotargeting of CIS–PT to human Epidermoid Carcinoma KB using the Avidin–Biotin System", *Int. J. Cancer*, 48:243–256, (1991).

Schechter et al., Renal accumulation of streptavidin: Potential use for targeted therapy to the Kidney *Kidney Int.*, 47:1327–1335, (1995).

Schwartz et al., "The Hepatic Asialoglycoprotein Receptor", *CRC Crit. Rev. Biochem.*, 16:207–223, (1984).

Schwartz et al., "Proteins Containing Reductively Aminated Disaccharides", *Archives Biochem. Biophys.* 181:542–549, (1977).

Taylor et al., "Contribution to Ligand Binding by Multiple Carbohydrate–recognition Domains in the Macrophage Mannose Receptor", *J. Biol. Chem.*, 267:1719–1729, (1992).

Wadhawa et al., "Targeted Gene Delivery with a Low Molecular Weight Glycopeptide Carrier", *Bioconjugate Chem.* 6:283–291, (1995).

Wilchek et al., "The avidin–biotin complex in immnology", *Immunology Today*, 5:39–43, (1984).

Wilchek et al., "The Avidin–Biotin Complex in Bioanalytical Applications", *Analytical Biochemistry*, 171:1–32 (1988).

Wilchek et al., "Avidin–biotin technology ten years on:has it lived up to its expections?", *Trends. Biochem. Sci.*, 14:408–412, (1992).

Wilson et al., "Hepatocyte–directed Gene Tranfer in Vivo Leads to Transient Improvement of Hypercholestererolemia in Low Density Lipoprotein Receptor–deficient Rabbits", *J. Biol. Chem.*, 267:963–967 (1992).

Wu et al., "Liver–directed gene delivery", *Adv. Drug Delivery Reviews*, 12:159–167, (1993).

\* cited by examiner

MODIFIED AVIDIN-TYPE MOLECULES AS TARGETING AGENTS FOR THE LIVER AND CELLS OF THE RETICULOENDOTHELIAL SYSTEM

CROSS-REFERENCE TO RELATED APPLICATIONS

This is a continuation-in-part of PCT application PCT/US96/20333, filed Dec. 20, 1996, which contents are herein incorporated by reference.

FIELD OF THE INVENTION

The present invention relates to novel derivatives of avidin-type molecules, particularly to avidin-type molecules modified with 2,4,6-trinitrophenyl (TNP) or lactosyl (Lac) groups, to antigen-antibody complexes of avidin-type molecules, and to compositions comprising them for targeted diagnostic and therapeutic treatment of the liver and the reticuloendothelial system.

BACKGROUND OF THE INVENTION

Drug delivery, using targeting systems wherein a drug or radioactive isotope are coupled to a specific targeting vehicle, has been studied for both therapeutic and diagnostic potentials. For the treatment of tumors, for example, targeting of drugs has been carried out via antibodies where the drug-antibody immunoconjugate is expected to localize specifically at a particular tumor cell. Limited specific uptake of immunoconjugates by human solid tumors was found to be the major limitation to drug or isotope immunotargeting, and therefore alternative vehicles for drug delivery other than antibodies showing specific affinity to a given tissue or organ, have been subject of further studies, such as, for example asialoglycoproteins for targeted delivery of small or large molecules to hepatocytes (Wu and Wu, 1993).

Streptavidin, a 52–60 kDa tetrameric non-glycosylated neutral protein which is a truncated form of the native streptavidin of *Streptomyces avidinii*, carries one biotin-binding site per monomer with a remarkably strong binding affinity to biotin (Chaiet and Wolf, 1964). The native, post-secretory form of streptavidin is larger and has a MW of 72 kDa (18 kDa per subunit). This native streptavidin molecule degrades rapidly to the stable 52–60 kDa streptavidin and can only be identified under special conditions. Bayer et al. (1989) reported that the native streptavidin undergoes proteolytic degradation during isolation to a truncated form with a molecular size of about 14 kDa per subunit, which is the commercial 52–60 kDa form of streptavidin known and recognized in the art. The truncation is effected through the cleavage of 12–14 amino acid residues at the N-terminal and up to 18 residues at the C-terminal end of each subunit. The 18 kDa streptavidin subunit was found to be sensitive to the action of several commercially available proteolytic enzymes, but once streptavidin (truncated form of the native molecule) is formed, it is remarkably stable to proteolytic activity (Wilchek and Bayer, 1989).

Streptavidin is similar in structure and biotin-binding properties to its counterpart avidin, a positively charged egg-white glycoprotein. The biotin-binding affinity of these two proteins is the highest recorded for any protein-ligand interaction ($10^{15}$ $M^{-1}$). Both proteins are tetramers containing one biotin-binding site per subunit and have similarity in a series of short interrupted segments (Green, 1975; Argarana et al., 1986), but they differ from each other in charge and glycosylation as well as in general primary sequence. Resistance to proteolytic enzymes is shared by both streptavidin and native avidin.

The streptavidin- and avidin-biotin complexes have provided extremely useful and versatile intermediates in a variety of biological and analytical systems (Wilchek and Bayer, 1984; Wilchek and Bayer, 1988). In principle, biotin coupled to a large variety of molecules can be recognized by avidin or streptavidin, either in their unmodified form or when coupled to various reporter probes, such as fluorescent dyes, radioactive elements, enzymes or immobilized matrices. Later, the use of these two systems has been extended to include different in vivo procedures, such as radioimmunodetection (Hnatowich et al., 1987) and immunotargeting (Longman et al., 1995). The present inventors have previously shown indirect immunotargeting of cisplatin to human epidermoid carcinoma using the avidin-biotin system (Schechter et al., 1991).

Biodistribution studies in mice comparing radioiodinated ($^{125}$I)-avidin, ($^{125}$I)-native streptavidin and ($^{125}$I)-streptavidin showed that, at 24 h, native streptavidin had a normal clearance pattern from all organs with retention levels of 1–10% of total injected dose per gram tissue (%/g) whereas avidin was cleared at a faster rate and was in the range of 0.2–3%/g (Schechter et al., 1990). In contrast, streptavidin exhibited a remarkable and prolonged accumulation in the kidney with uptake levels of 70–80% of the injected dose/g tissue (%/g), mostly confined to the kidney cortex, for a period of 3–4 days following i.v. or i.p. injection, whereas its levels in other organs was low (0.3–4%/g) (Schechter et al., 1995). In terms of organ accumulation, 15% of the total injected dose of streptavidin was accumulated in each kidney, an organ comprising only 1% of the total body weight. Similar results of organ accumulation were also obtained for rats and rabbits (Schechter et al., 1995).

Addition of exogenous biotin did not reduce kidney uptake and did not affect streptavidin biodistribution to other organs (Schechter et al., 1990), excluding the possibility that streptavidin accumulation occurs due to interaction in the kidney with free biotin or with biotinylated proteins. The observation that native streptavidin and avidin, both displaying biotin-binding affinity, did not accumulate in the kidney, also excludes the possibility that biotin or biotinyl groups in this organ serve as the major anchor for streptavidin accumulation.

Avidins are enzyme resistant carriers (Hiller et al., 1991; Ellison et al., 1995) that can serve to provide selective and prolonged organ accumulation to ensure prolonged maintenance of these carriers in the target organ. Streptavidin itself (52–60 kDa) is accumulated in the proximal tubule of the mouse kidney for 3–4 days. This is due to processing of low MW proteins (<64 kDa) which generally undergo tubular endocytosis and active lysosomal degradation. The exceptional long-term sequestration of streptavidin in the kidney is attributed to its unique resistance to enzymatic degradation (avidin, which is of a higher molecular size, 67 kDa, did not accumulate in the kidney and was rapidly cleared from the circulation and tissues).

Chemical modification of macromolecules can change the in vivo disposition profile of these macromolecules and lead to receptor-mediated targeting or other types of cellular uptake in the target organ targeted by these potential macromolecular homing devices. Hepatotropic markers which are receptor specific to terminal β-D-galactose or N-acetyl-α-D-galactosamine present on mammalian parenchymal cells (hepatocytes) have been reported earlier (Ashwell and Hartford, 1982; Schwartz, 1984). The high affinity interaction with this receptor triggers efficient internalization of circulating asialoglycoproteins (ASGP), synthetic glycosylated proteins, or other macromolecules (neoglycoproteins or neoglycoconjugates) modified with saccharides (Lee and Lee, 1994). Thus, carbohydrate receptor-mediated targeting to parenchymal (via terminal β-D-galactose or N-acetyl-α-D-galactosamine) and non-parenchymal (via terminal N-acetylglucosamine or mannose; Stahl and Schlesinger, 1989; Magnusson and Berg, 1989) cells of the liver has shown great promise as a potential delivery method using receptor-mediated endocytosis. The advantages of this system arise from the high affinity of the receptor for the ligand and the rapid recycling of the receptor molecule.

Natural asialoglycoproteins (ASGP), such as asialoorosomucoid and asialofetuin, were employed first, but later on, synthetic glycosylated proteins (neoglycoproteins) were used as prototypes of carrier systems. The rapid clearance of these carriers yielded attempts to slow down their degradation in order to achieve gradual but predominant accumulation in the target tissue. One of the approaches used chemical modification with biologically inert macromolecules, such as polyethyleneglycol (PEG). However, PEG conjugation was found to result in prolonged plasma retention due to reduction of interaction with tissues (Civitico, 1990; Crance, 1990).

Most of the systems developed for drug targeting utilize macromolecular carriers armed with targeting ligands recognized by specific cell types. Certain targeting ligands are known, the most common are terminal saccharide residues recognized by receptors on liver parenchymal (Gal and GalNac of asialoglycoproteins, Ashwell et al, 1982) non-parenchymal cells (GluNac and Man, Taylor et al, 1992), B-cells (Lasky et al, 1989) or endothelial cells (Bevilacqua et al, 1989). Recent developments in peptide chemistry and molecular biology yielded diverse peptide libraries consisting of numerous random peptide sequences (Pasqualini et al, 1996). Peptides with specific biological activity capable of mediating selective localization in tissues such as lung (Johnson et al, 1993) or lymphocytes (Cepek et al, 1994) have been obtained. An important example is the recently reported families of angiogenesis suppressing/inducing integrins that suppress or encourage the generation of new blood vessels (Varner et al, 1996; Folkman, 1996). These proteins are adhesion receptors not present in normal tissue but appear on endothelial cells of blood vessels of neovasculating areas. Since neovascularization is typical of malignant tissues at a certain stage, substances that interact with integrins might be considered as tissue markers for contrast agent delivery to blood vessels in neovaculating tumors (Brooks et al, 1994; Arap et al, 1998). Systematic screening of chemically-modified proteins (Neurath et al, 1995; Fujita et al, 1994) also yielded products recognized selectively by specific cells, for example, aromatic acid anhydrides that block CD4 cell receptors for HIV-1. Several systems were described that utilize macromolecular carriers armed with targeting ligands recognized by specific cell types (Monsigny et al, 1994; Hashida et al, 1995).

Tissue-targeting research and practice also utilize several alternative approaches. Some rely on physiochemical properties leading to passive uptake and accumulation, such as inherent accumulation of the agent by the target tissue (e.g., iodine by the thyroid). An important mechanism is the retention and enhanced permeability (EPR) phenomenon whereby molecules of a certain size may diffuse through blood vessels in areas of neovascularization as in malignant tissues (Matsumura et al, 1986; Duncan et al, 1996).

The intense activity in the field of targeting drugs to specific organs, tissues or cells (Matsumura et al, 1986) have yielded a variety of carrier systems such as pro-drugs, liposomes, e.g., sterically stabilized liposomes (SSL) (Kedar et al, 1994) or polymers, both natural and synthetic. The carrier conveys the drug to the specific tissue (via antibody or a tissue marker) where the drug executes the therapy. While tissue specific homing has been demonstrated in various studies, most macromolecular carrier systems are rapidly eliminated in the host, and consequently, these systems do not seem to exhibit a residence time necessary for achieving a therapeutic effect.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

Abbreviations

The following abbreviations are used throughout the specification:

ASGP asialoglycoproteins
Av avidin
B biotinyl
BOC butyloxy
BSA bovine serum albumin
BT biotinyl-tyrosine
BT1 biotinyl-diaminopropyl-L-tyrosine
CDDP cis-dichlorodiamine platinum (cisplatin)
CMdex carboxymethyl dextran
DAP 1, 3-diaminopropane
DCC dicyclohexylcarbodiimide
DMF dimethylformamide
DTPA DTPAdiethylenetriaminepentaacetic acid
DDW double-distilled water
EDCI 1-ethyl-3(3-dimethylaminopropyl)-carbodiimide
FUR 5-fluorouridine
Gd Gadolinium
Lac lactosyl
MRI magnetic resonance imaging
NHS N-hydroxysuccinimide
NL Neutralite
Ov ovalbumin
PBS phosphate-buffered saline
RES reticuloendothelial system
St streptavidin
TABAD thermophilic anhydride Brokii alcohol dehydrogenase
TNBS 2,4,6-trinitrobenzenesulfonic acid
TNP 2,4,6-trinitrophenyl

SUMMARY OF THE INVENTION

It has now been found in accordance with the present invention that a simple modification of the avidin or streptavidin molecule leads to a change in the biodistribution pattern thereof. Thus, the reaction of 2,4,6-trinitrobenzenesulfonic acid (TNBS) with ε-amino groups of lysine residues in streptavidin or the lactosylation of ε-amino groups of lysine residues in streptavidin abolishes the accumulation of the modified streptavidin in the kidney and shifts it to the liver. The trinitrophenyl (TNP)-streptavidin product has increased liver levels as early as 1.5 h following injection, which peaks at 24–48 h to 30–50%/g tissue, and then slowly declines. The TNP-streptavidin product persists in the liver at relatively high levels for several days. Avidin, which in its native form is rapidly eliminated from all organs, also accumulates in the liver following TNP-modification, while TNP-modification of normally-cleared proteins, such as BSA, RNase, immunoglobulin (IgG) and TABAD, a relatively enzyme-resistant protein, does not result in accumulation in the liver or in any other organ at 2.5 h or 30 h. The TNP-modified avidin-type product accumulates preferentially in the Kupffer cells of the liver.

Lactosylated streptavidin is also found to accumulate in the liver at a high level that persists for several days although lactosylated avidin exhibits only short term accumulation in the liver. The lactosyl-modified avidin-type product accumulate preferentially in the liver hepatocytes.

In addition, it has also been found that when streptavidin is complexed to an anti-streptavidin antibody, the biodistribution pattern in tissues is modified and exhibits high and prolonged levels of the antigen-antibody complex in the spleen and liver, and preferentially in the cells of the reticuloendothelial system.

The present invention thus provides an avidin-type molecule, selected from native egg white avidin, recombinant avidin, deglycosylated forms of avidin, streptavidin recombinant streptavidin, and derivatives of all of the above molecules that are derivatized at sites other than the lysine and essential tyrosine residues, which avidin-type molecule is modified at the $\epsilon$-amino groups of lysine residues with a 2,4,6-trinitrophenyl group (TNP) or with a lactosyl group, or is in a complex with an avidin-type molecule-specific antibody.

The present invention further provides radiolabeled forms of the TNP-and lactosyl-modified avidin-type molecules or of the antibody-avidin-type molecule complexes, complexes of the TNP- and lactosyl-modified avidin-type molecules or antibody-avidin-type molecule complexes of the present invention with biotinylated therapeutic, biotinylated diagnostic, biotinylated carrier-therapeutic, or biotinylated carrier-diagnostic agents, and conjugates of the TNP- or lactosyl-modified avidin-type molecules or antibody-avidin-type molecule complexes with therapeutic or diagnostic agents.

The present invention still further provides pharmaceutical compositions and methods for diagnosing and for treating hepatic disorders and disorders of the reticuloendothelial system.

BRIEF DESCRIPTION OF THE DRAWINGS

FIG. 18A) in comparison to complexes between radioiodinated TNP-BSA or TNP-St and &TNP Ab at 3 h and 24 h (FIG. 18B).

DETAILED DESCRIPTION OF THE INVENTION

Figure 1:
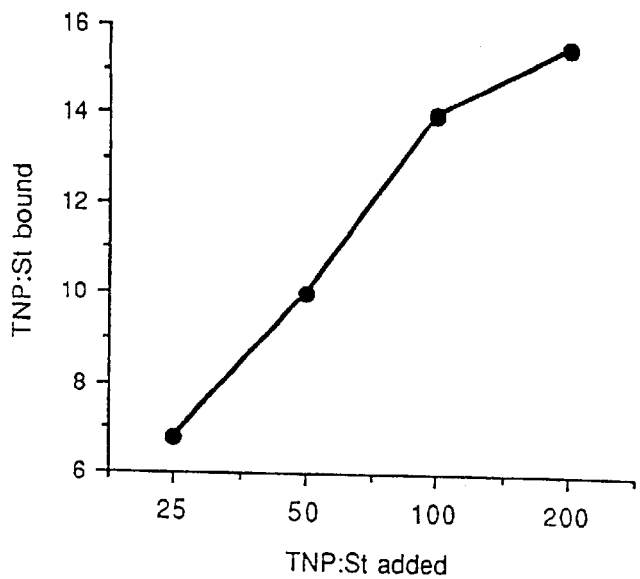
FIG. 1 shows the substitution ratio of TNP-St (TNP:St bound) obtained as described in Example 1.

The present invention relates to the surprising discovery that specific tissue markers like avidin-type molecules modified with TNP for liver Kupffer cells or modified with lactosyl groups for liver hepatocytes, as well as antibody-avidin-type molecule complexes for reticuloendothelial system (RES), can be targeted to specific and distinct tissues for a long period of time. The change in biodistribution pattern of these avidin-type molecules to selectively target the liver, and to a smaller extent, the spleen, provides a vehicle for the delivery of radionuclides and other diagnostic or therapeutic agents for the diagnosis and treatment of hepatic disorders. The selective targeting to the RES provides a vehicle for the delivery of radionuclides and other diagnostic and therapeutic agents for the diagnosis and treatment of RES disorders.

The term "avidin-type molecule" as used throughout the present specification and claims refers to the native egg-white glycoprotein avidin and deglycosylated forms of avidin, to streptavidins produced by selected strains of Streptomyces, e.g., *Streptomyces avidinii,* either in their native 72 kDa or stable truncated 52–60 kDa forms, to recombinant avidin and recombinant streptavidin as well as to derivatives of the foregoing that are derivatized at sites other than lysine residues and essential tyrosine residues. The term "modified avidin-type molecules" as used throughout the present specification and claims refer to avidin-type molecules which are modified with either a 2,4,6-trinitrophenyl (TNP) group or a lactosyl group at the ε-amino group of lysine residues, or are in a complex with an antibody specific for the avidin-type molecule.

Some of these materials are commercially available, e.g., native avidin, deglycosylated avidins and streptavidin, or can be prepared by well-known methods (see Green, 1975 for preparation of avidin and streptavidin; Bayer et al. 1995, for preparation of deglycosylated avidin). Recombinant avidin and recombinant streptavidin can be prepared by standard recombinant DNA techniques, for example, as described by Chandra and Gray, 1990, and by Argarana et al., 1986, for recombinant avidin and recombinant streptavidin, respectively. Unless otherwise specified, the terms "streptavidin" or "recombinant streptavidin" as used in the present examples and elsewhere in the present specification refer to any purified or commercial form of streptavidin that has a molecular weight of 52–60 kDa.

Derivatives of avidin-type molecules according to the present invention are intended to include those that are derivatized at sites other than the lysine and essential tyrosine residues, such as derivatives obtained via derivatization of arginine residues. Two different derivatives of avidin which were derivatized in this manner are commercially available. One avidin derivative, ExtrAvidin®, can be obtained in various functionally derivatized or conjugated forms from Sigma Chemical Company (St. Louis, Mo., USA). A second avidin derivative, NeutraLite Avidin® (hereinafter designated NL-Av), a product of Belovo Chemicals, Industrial Area 1, Bastogne, Belgium, is a deglycosylated form of avidin, which was obtained enzymatically, and exhibits a neutral pI and bears free lysine groups for further derivatization.

Radiolabeled forms of the modified avidin-type molecules and derivatives thereof of the present invention for use in therapy or in radioimaging include, as non-limiting examples, radionuclides, such as $^{111}$In, $^{125}$I, $^{131}$I and $^{99m}$Tc. The radiolabeled forms, which are preferably radioiodinated forms, are prepared by standard methods, e.g., by reaction of the modified avidin-type molecule with a salt, such as Na$^{125}$I.

Gadolinium (Gd) complexes are the most preferred reagents for enhanced dynamic MRI. According to the present invention, complexes of biotinyl-carrier-diagnostic agents with modified avidin-type molecules and derivatives thereof for use in MRI are provided where a modified avidin-type molecule is linked to Gd via a biotinylated carrier. A suitable carrier is poly-L-lysine to which is attached a Gd complex, such as Gd-DTPA or phosphonated Gd-DTPA (Adzamil et al., 1991). Diagnostic agents of relatively low sensitivity, such as Gd, are preferably complexed to any suitable carrier which permits a higher load of the diagnostic agent per unit of a complex. However, if the diagnostic agent can be detected at low levels in the targeted cells or organ, it will be appreciated that the diagnostic agent does not require a carrier as part of the complex. If the diagnostic agent is sufficiently sensitive for imaging or scanning procedure, it can be biotinylated directly to the modified avidin-type molecule, in the absence of carrier, or in appropriate situations, can be directly conjugated to the modified avidin-type molecule. The biotinyl-carrier-diagnostic agent may also be $^{99m}$Tc complexed to DTPA and linked via biotinyl-poly-L-lysine to the modified avidin-type molecule. The Gd or $^{99m}$Tc complex with DTPA is preferably prepared by first complexing biotinyl-poly-L-lysine-DTPA to the modified avidin-type molecule and then labeling with Gd or $^{99}$mTc. Other non-limiting examples of biotinyl-carrier-diagnostic agent include a macromolecular carrier linked to a heavy metal diagnostic/contrast agent via a metal binding group. The diagnostic/contrast agent for detection techniques based on X-ray attenuation in the imaged body (e.g., 2D digital radiography, CT, dual energy and image subtraction, "positive" and "negative" imaging, etc.) can be an element with an X-ray attenuation threshold in the relevant energy range for the specific radiography technology, e.g., Zr, in the case of mammography. At the X-ray attenuation threshold, there is an abrupt change or discontinuity in the X-ray attenuation coefficient with respect to X-ray energy. All elements with atomic number Z in the range of 33–50 exhibit such an X-ray attenuation threshold in the 10–30 keV X-ray energy range. When an energy range above 30 keV is used in radiography, an element with Z above 50 is used for its property of having an X-ray attenuation threshold in the appropriate X-ray energy range.

The diagnostic/contrast agent may be any non-toxic (in free or in bound form) organic or inorganic compound of a heavy element with Z=75–92, preferably a heavy metal selected from Pt, Au and Tl, and the macromolecular carrier selected from liposomes and natural or synthetic polymers. The heavy metal compound may be attached to the natural or synthetic polymer through a metal-binding group or ligand containing nitrogen, nitrogen-oxygen or sulfur atoms, such as thiol, hydrazido, piperazine and the like, or the heavy metal compound may be complexed to the polymer through a metal-chelating group, such as iminodiacetic, EDTA, EDPA, hydroxyquinoline, hydroxamic acid and the like.

Two types of macromolecular carriers can be used for heavy metal diagnostic/contrast agents. The first is a conjugate of the polymer with a metal binding group to which a heavy metal is attached. This general type is preferable for non-targeted delivery into cancerous sites by physical entrapment processes, such as those occurring in neovascularization sites of tumors. The second type is a conjugate of the polymer with a targeting ligand (tissue marker), in addition to the metal binding group to which a heavy metal is attached. The role of the targeting ligand is to direct the whole conjugate to a specific tissue via the affinity interaction of the targeting ligand to a given epitope on the specific cell. Certain targeting ligands/tissue markers are known, as presented in Table 1, and these targeting ligand/tissue markers can be used in place of TNP or lactosyl groups to preferentially direct the modified avidin-type molecule according to the present invention to the specific tissues indicated in Table 1.

TABLE 1

Tissue Markers (Examples)

| Tissue | Marker | Reference |
|---|---|---|
| Liver Hepatocytes (Asialoglycoprotein Receptor) | Gal, GalNac | Ashwell et al (1982) |
| Liver Kupffer Cells | Man, GluNac, Fuc | Taylor et al (1992) |
| B Cells (IgE Fc Receptor) | Gal | Kikutani et al (1986) |
| Leukocytes L-selectin) | Fuc, Sialic acid | Lasky et al (1989) |
| Endothelial Cells (E-selectin) | Fuc, Sialic acid | Bevilacqua et al (1989) |
| Platelets (P-selectin) | Fuc, Sialic acid | Johnston et al (1989) |
| Lung and Liver Macrophates | Man, Fuc | Taylor et al (1992) |
| Lung | Endothelial Marker | Pokutta et al (1994) |
| Brain[1] | Ser-Arg-Leu (SRL) Containing Peptide | Pasqualini et al (1996) |
| Kidney Blood Vessels | CLPVASC Peptide | Pasqualini et al (1996) |
| Tumor Blood Vessels | Arg-Gly-Asp (RGD) and Asn-Gly-Asp (NGD) Containing Peptides | Arap et al (1998) |
| CD4 Cell Receptors for HIV-1 | 3-hydroxyphthalic and Trimellitic Anhydrides | Neurath et al (1995) |

[1]Many cell adhesion receptors recognize simple sequences that can be reproduced as synthetic peptides homing to these cells. Peptides capable of binding to cell adhesion receptors, such as integrins, can be used as mediators for cell or tissue targeting. Factors such as EGF, VEGF, MHS, etc. can also serve for specific tumor targeting to the specific receptors (for these factors) that are overexpressed on certain tumor cells.

In order to select a suitable delivery system according to either type of targeting system described above, biodistribution of the metal-macromolecular carrier conjugate provides information regarding its specific sites of accumulation, metal uptake kinetics and saturation. To provide biodistribution data, the polymer is charged with several tyrosyl residues for radioiodination, the radiolabeled agent is then administered intravenously into mice, and at set time intervals, blood and organs are analyzed for biodistribution parameters (Schechter et al, 1996). Determination of the actual metal accumulation can be done by atomic absorption spectroscopy, XRF and ICPS (inductively coupled plasma spectroscopy) analysis of tissue samples. Experiments are directed at both tissue accumulation for "negative imaging" and tumor accumulation for "positive imaging".

The preferred systems for delivery of heavy metal contrast agents according to the present invention are macromolecules carrying a heavy metal as defined in the present invention. Such a macromolecule that will be defined for the purpose of this invention as a "macromolecular system" is composed of (a) a suitable macromolecular carrier, (b) a metal binding group as a pendant group, and (c) a heavy metal salt or complex. The metal salt or complex will be part of the macromolecular system due to attachment via the metal binding ligand. The scientific literature, including patents, teaches many ways to bind a metal salt or metal complex to a macromolecular carrier, including the present inventors' own publications (Schechter et al, 1996; Schechter et al, 1986a; Schechter et al, 1986b; Schechter et al, 1987a; Schechter et al, 1987b; Schechter et al, 1989a; Arnon et al, 1989a) which show how to bind platinum and platinum group metal (including gold) to polymeric carriers. The literature also teaches us how to bind metal ions to polymers for pharmaceutical uses (Dunn et al, eds., 1991). Of particular interest for the present invention are polymer carriers, such as, for example, the polymers described in Duncan et al (1996) and Pimm et al (1996), polymers which display selective delivery or accumulation in the target tissue, e.g., polymethacrylic acid in neovasculating regions such as in tumors, as well as polymers modified with specific tissue markers, including address molecules with known tissue or organ specificity, such as hormone receptors that are over-expressed in certain types of breast cancer (Pimm et al, 1993). The chemical binding between the contrast agent and the macromolecular carrier should be strong enough to prevent metal release to avoid the poisonous effects of the heavy metal and to allow high agent loading capacity to enable minimal carrier doses.

Any hepatic disorder may be treated with the radiolabeled forms, conjugates or complexes according to the present invention. Examples of these hepatic disorders are: inflammatory disorders of the liver including, but not limited to, acute and chronic viral hepatitis A, B and C; neoplastic diseases including both primary liver tumors, e.g., hepatocellular carcinoma, and liver metastases; and genetic disorders, e.g., Wilson's disease, hemochromatosis, glycogen storage diseases, familial hypercholesterolemia caused by LDL-receptor deficiency, phenylketonuria caused by phenylalanine hydroxylase deficiency.

Any suitable antiviral or chemotherapeutic agent or a combination thereof may be used as a therapeutic agent according to the present invention. Examples of such antiviral agents are interferon alpha and beta as indicated for treatment of hepatitis C (Di Bisceglie et al., 1992 and 1993; Kakumu et al., 1993), ribavirin disclosed for treatment of hepatitis A, B and C (Crance et al., 1990; Civitico et al., 1990; Di Bisceglie et al., 1992; Kakumu et al., 1993), and vidarabine for treatment of hepatitis B (Ouzan et al., 1987). Examples of antineoplastic agents suitable for treatment of liver carcinomas are doxorubicin, mitomycins, cisplatin (CDDP), fluorouracil, tiazofurin or a combination of tiazofurin and ribavirin (Natsumeda et al., 1988). Most of these antiviral and antineoplastic agents display adverse side effects and are of limited use in conventional treatments. However, targeting of these agents to the liver according to the present invention is expected to improve the effectiveness of these treatments.

The antiviral or anticancer therapeutic agent may be covalently linked to the modified avidin-type molecule as a conjugate, or it may be biotinylated and then complexed with the modified avidin-type molecule, or it may be linked to a biotinylated carrier and then complexed with the modified avidin-type molecule. The above complexes are very stable due to the high affinity of the modified avidin-type molecule binding sites for the biotin of the biotinylated agents or carriers.

Hepatic gene therapy may provide a therapeutic approach for various inherited disorders by introducing a normal gene and its associated function into hepatic cells. For this purpose, the therapeutic agent in a complex of a biotinyl-carrier-therapeutic agent is a suitable DNA sequence for the treatment of a genetic disorder, where the DNA is complexed with a suitable carrier, e.g., poly-L-lysine or poly-L-lysine substituted with small ligands, such as carbohydrate moieties (Erbacher et al., 1995; Wadhawa et al., 1995), and using suitable vectors as described for gene therapy in general (Mulligan, 1993) and hepatic gene therapy in particular (Wu and Wu, 1993; Ledley, 1993; Ledley et al., 1993; Wilson et al., 1992).

Any suitable carrier used in biological systems may be biotinylated and complexed with or coupled to the therapeutic or diagnostic agent and complexed to the modified avidin-type molecule as well as derivatives thereof. Examples of such carriers are: carbohydrates, e.g., dextran, carboxymethyl dextran; polyamino acids and copolymers of amino acids, e.g., poly-L-lysine, polyalanine, polyglutamic acid, polyalanine/lysine/tyrosine and polytyrosine/alanine/glutamic acid copolymers; and synthetic polymers, such as divinyl ether/maleic anhydride copolymer.

According to the present invention, modification of streptavidin with TNP or lactosyl groups shifted its accumulation to the liver, and in particular, to liver Kupffer cells for TNP groups, and to liver hepatocytes for lactosyl groups. In biodistribution studies, retention of $^{125}$I-TNP-St in the liver reached levels of 30–50%/g at 24 h (retention level of total injected dose per gram of tissue) during a period of 3–4 days, while levels in other organs or tissues were less than 5%/g (in the spleen it was somewhat higher), indicating that 40–60% of the injected dose was accumulated in the liver, which is an organ that constitutes less than 4–5% of total body weight. Avidin in its native form is rapidly cleared from all organs, but TNP-Av was found to be accumulated in the liver (30–40%/g) and to some extent in the spleen (10–15%/g). TNP-NL-Av also accumulated in the liver, but its spleen accumulation was further increased (up to 20%/g). Lactosylated streptavidin (Lac-St) was also found to accumulate in the liver. Thus, TNP-St, TNP-Av, TNP-NL-Av, and Lac-St may serve as hepatic targeting devices for delivery of various therapeutic or diagnostic agents to the liver.

Furthermore, antigen-antibody complexes formed of an avidin-type molecule and an antibody that binds to the avidin-type molecule can be used to target cells of the reticuloendothelial system (RES). It is believed that the liver and spleen RES is involved in the uptake of antigen-antibody complexes via Fc-receptors on macrophages. Accordingly, the antibody used in the antigen-antibody complex can be an immunoglobulin molecule of any isotype. It is also intended that chimeric or single chain antibodies be included as antibodies for forming the avidin-type-molecule-antibody complex of the present invention.

The present invention thus provides pharmaceutical compositions for the diagnosis of hepatic disorders or disorders of the RES comprising a radiolabeled form of a modified avidin-type molecule, or a complex of a modified avidin-type molecule with a biotinyl-diagnostic agent or with a biotinyl-carrier-diagnostic agent, or a conjugate of a modified avidin-type molecule with a diagnostic agent, and a pharmaceutically acceptable carrier. Correlating altered accumulation or distribution patterns of these labeled/tagged modified avidin-type molecules with pathological states may improve imaging or scanning procedures. Thus, according to the present invention, radiolabeled $^{125}$I-TNP- or $^{125}$I-lactosyl-St and -Av were shown to be targeted to the liver, as discussed above, and Gd was shown to be targeted to the liver via TNP-St, i.e., via the complex TNP-St-B-(Lys)l$_9$-DTPA-Gd, demonstrating that this complex can be used for magnetic resonance imaging (MRI) of the liver. As each of the three type of modifications disclosed herein direct the composition preferentially to different cells of the liver, a particular modification can be chosen whenever any given application may require specificity to particular types of cells in the liver.

The invention further provides pharmaceutical compositions for the therapeutic treatment of hepatic disorders or disorders of the RES and comprises a radiolabeled form of a modified avidin-type molecule, a conjugate of a modified avidin-type molecule with a therapeutic agent, or a complex of a modified avidin-type molecule with a biotinyl therapeutic agent or with a biotinyl-carrier therapeutic agent, and a pharmaceutically acceptable carrier.

Thus, in accordance with the present invention, TNP-St was shown to target therapeutic doses of the radionuclide $^{125}$I to the liver which then persisted in this organ for 10 days at considerably high levels.

The capacity of TNP-St, and TNP-Av to serve as targeting vehicles for various biotinylated therapeutic agents, wherein these therapeutic agents are either linked directly or via a carrier to the biotinyl residue, was demonstrated as follows:

(a) TNP-St and TNP-Av could target a low MW ligand, such as biotinyl-tyrosine (BT) (as shown in Examples 6 and 7), or a high MW ligand carrier, such as carboxymethyl dextran (CMdex) (T-10) and (T-40), charged with 1–3 mol BT$_1$/mol CMdex, (as shown in Example 8) to the liver. The targeted ligand was monitored through the radioiodinated $^{125}$I-BT at the tyrosine residue;

(b) the chemotherapeutic drug 5-fluorouridine (FUR) could be targeted to the liver via TNP-St/Av by attaching FUR to $^{125}$I-BT$_1$-CMdex-hydrazide (T-40), as shown in Examples 9 and 10. Oxidized FUR was coupled to NH$_2$ of the hydrazides as confirmed by 86% reduction in NH$_2$ content following attachment of FUR. Biodistribution was either monitored as described above or by trace labeling FUR with [$^3$H] uridine, in which case direct accumulation of the drug in the liver could be demonstrated by monitoring [$^3$H] radioactivity in tissue extracts;

(c) the chemotherapeutic drug, cisplatin (CDDP), was targeted to the liver by complexing it to $^{125}$I-BT$_1$-CMdex as shown in Example 11. Targeting to the liver of Pt-$^{125}$I-BT$_1$-CMdex via TNP-St and TNP-Av was demonstrated by radioactive monitoring of the drug-carrier as described above. Specific liver accumulation of CDDP could be demonstrated by atomic absorption spectrometry which detects the Pt metal in the tissues. Such measurements were in general agreement with the radiodistribution results showing high accumulation of CDDP in the liver (over a time period lasting at least 15 h after injection) vs. low accumulation in other organs. Moreover, whereas significant amounts of the targeted drug were detected in the liver even at 15 h following injection, no CDDP could be found at 2 h after the injection of an even higher dose of the free drug.

Other chemotherapeutic as well as antiviral drugs, such as doxorubicin, mitomycin, tiazofurin, interferon-alpha, interferon-beta, ribavirin and vidarabine, can be used in the pharmaceutical compositions of the present invention. The preferential and prolonged retention of TNP-Av or TNP-St in the liver as well as utilization of coupling procedures designed to permit programmed release of the drug, facilitates novel treatment strategies for liver disorders, viral diseases and malignancies. Appropriate attachment of the therapeutic agent to the targeting molecules to facilitate its continuous release is expected to enable localized delivery and to maintain prolonged exposure to the drug. Since TNP-Av or TNP-St accumulation are almost exclusively confined to the liver, a decrease in systemic toxicity is expected and administration of a higher dosage of the drug may be feasible. Likewise, Lac-St and Lac-Av can also serve as targeting vehicles for biotinylated therapeutic agents.

When the therapeutic agent is a DNA molecule, the foreign DNA sequence is targeted to the liver by any of the proposed methods for targeted delivery and expression of genes (Mulligan, 1993) and for hepatocytes in particular (Ledley et al., 1993; Ledley, 1993; Wu and Wu, 1993; Wilson et al., 1992; Erbacher et al., 1995).

The invention further relates to a method of diagnosing hepatic disorders or disorders of the RES which involves administering to a patient a radiolabeled form of a modified avidin-type molecule or a complex of a biotinyl-diagnostic agent or a biotinyl-carrier-diagnostic agent with a modified avidin-type molecule, or a conjugate of a diagnostic agent with a modified avidin-type molecule, and scanning the liver by standard scanning procedures, e.g., methods of nuclear medicine or radio-imaging or computerized tomography to detect radioactive label or the biotinylated tag. Modified avidin-type molecules are not only effective as contrast agents in the detection of liver morphological abnormalities of the liver and RES but are also effective as functional reagents, where changes in accumulation of these agents are indicative of a damaged liver or RES. This is particularly important for the diagnosis of liver tumors, where only certain intrahepatic benign or malignant tumors can be safely diagnosed by a single method on the basis of their characteristic pattern.

In another embodiment of the invention, a two-step diagnosis method is provided in which the modified avidin-type molecule is first injected and accumulated in the liver or RES, followed by the administration of the biotinylated diagnostic agent or the biotinylated-carrier-diagnostic agent.

The present invention further relates to a method of treating a hepatic disorder or disorder of the RES which involves administering to a patient in need thereof an effective amount of a radiolabeled form of a modified avidin-type molecule, or of a conjugate of a modified avidin-type molecule with a therapeutic agent or of a complex of a modified avidin-type molecule with a biotinyl-therapeutic agent or with a biotinyl-carrier-therapeutic agent.

In one embodiment of the method of treating hepatic or RES disorders, the injection of the modified avidin-type molecule is followed by administration of the biotinylated therapeutic agent or biotinylated-carrier-therapeutic agent. The two step method is particularly of interest in gene therapy.

Homing of modified avidin-type molecules to the liver or the RES is expected to be superior to targeting with immunotargeted systems in terms of local enrichment, dose and duration. Ligands can be attached to avidin and streptavidin via conventional protein-ligand conjugation methods. However, a major advantage of the modified avidin-type molecules is that, in addition to their high concentration in the liver or the RES, and their specific targeting to specified cells thereof, they are also equipped with extremely efficient built-in binding units, namely, their binding sites for biotin or for any biotinylated compound.

Modified avidin-type molecules, and particularly, lactosylated- and TNP-St/Av and antibody-avidin-type complexes will thus very effectively bind a large variety of biotinylated ligands, such as proteins (antibodies, enzymes), antiviral drugs, or carrier molecules for chemotherapeutic agents, radioactive compounds, fluorescent or MRI tags, DNA sequences and others. The ligand which is targeted to the liver, even if not delivered specifically to a given target cell, may be designed to allow for its sustained and continuous release by the inclusion of appropriate cleavable or dissociable moieties between the biotin and the reactive group, or between the drug and the carrier; otherwise, if needed, a stable bond can be employed. Biotinylated ligands also permit the use of a two-step localization approach in which the modified avidin-type molecule is first administered and allowed to accumulate in the liver or the RES, followed by injection of the biotinyl-ligand, which then homes in on the biotin-binding sites of the modified avidin-type molecules accumulated in the liver. Alternatively, modified avidin-type molecules charged with biotin groups by complexing it to di-biotin molecules (e.g., biotinyl-DAP-Tyr-biotin), or by attaching biotinyl groups to their lysine residues, can serve as targets for subsequent targeting of ligands attached to avidin-type molecules.

Whereas the total dose of a modified avidin-type molecule, whether radiolabeled, complexed, conjugated or in free form, to be administered in a method of diagnosing or treating hepatic disorders or disorders of the RES is preferred to be given in a single dose, the total amount of a modified avidin-type molecule may be administered in a single dose or in multiple doses. It is understood that the dosage administered will be dependent upon the age, sex, health, and weight of the recipient, frequency of treatment and the nature of the effect desired. The modified avidin-type molecule is administered in an amount which can target an effective amount of a radionuclide, a diagnostic agent or a therapeutic agent to the liver. Such an amount can be routinely determined by those of skill in the art in view of the examples provided in the present specification. The dosage is preferably in the range of 2.5 $\mu$g–1.5 mg/kg body weight in humans. It will be appreciated by those in the art that generally lower doses will be used in therapy and higher relative doses will be used in diagnosis.

Preparations for parenteral administration in the methods of the present invention, such as preferably by intravenous injection, include sterile aqueous and non-aqueous solutions, suspensions, and emulsions, which may contain suitable pharmaceutically acceptable vehicles containing excipients and auxiliaries which are known in the art. Such suitable pharmaceutically acceptable vehicles are well known in the art and are described, for examples, in *Remington's Pharmaceutical Sciences*, ed. A. Gennaro, 18th edition, 1990, Mack Publishing Co., Easton, Pa., a standard reference text in this field. For instance, formulations for intravenous administration may include sterile aqueous solutions which may also contain buffers, diluents and other suitable additives.

Having now generally described the invention, the same will be more readily understood through reference to the following examples which are provided by way of illustration and is not intended to be limiting of the present invention.

The materials and methods used in common in the examples are as follows:

(i) Materials. Streptavidin was a gift from Boehringer-Mannheim GmbH (Mannheim, Germany); avidin from S.C. Belovo (Bastogne, Belgium); and CDDP from Abic Company (Netanya, Israel). CMdex was prepared as previously described (Hurwitz et al., 1980). Biotin-NHS, EDCI, TNBS, t-butyloxycarbonyl (t-BOC) tyrosine and DCC were purchased from Sigma Chemical Company (St. Louis, Mo., USA), and DAP was purchased from Merck-Schuchardt (Munich, Germany).

(ii) Animals. Age-matched CD-1 male mice (6–12 weeks old) were used in the experiments.

Figure 2:
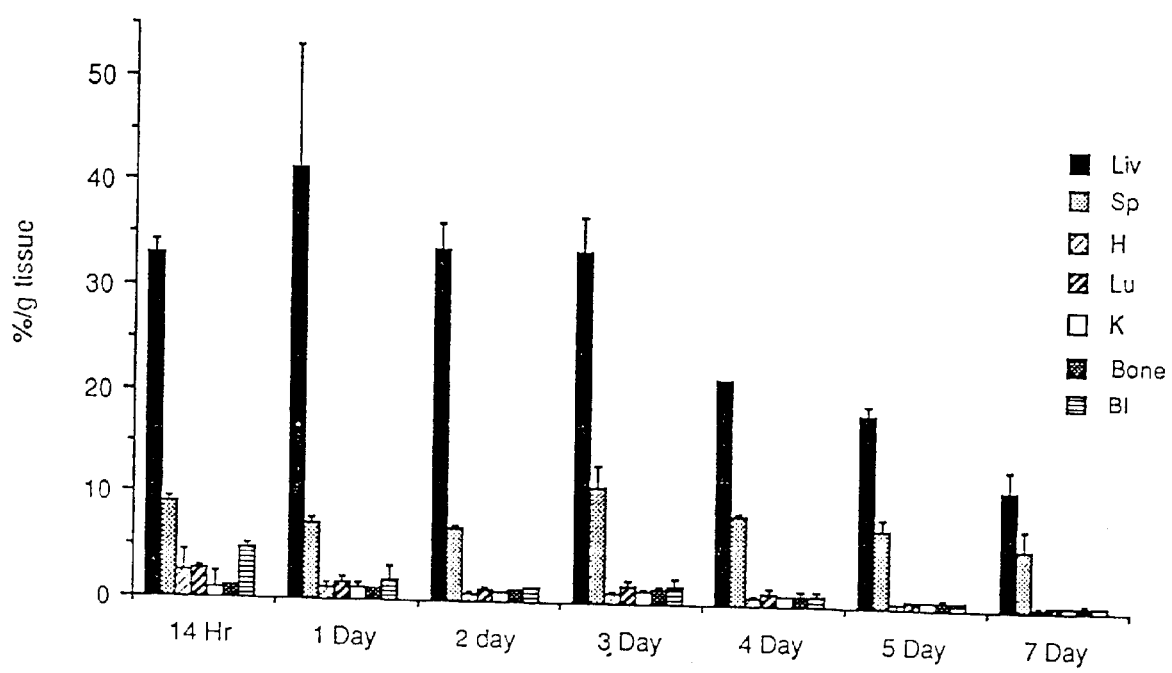
FIG. 2 shows the biodistribution of $^{125}$I-TNP-St in tissues of mice during a period of 7 days, as described in Example 2. Mice used in this figure and in the figures that follow are CD-1 male mice. Tissues used in this figure and in the figures that follow are designated as: H=heart; Lu=lung; Sp=spleen; Liv=liver; Kid=kidney; Bl=blood.

(iii) Biodistribution experiments. Groups of age-(6–12 weeks) and weight-matched male CD-1 mice were given intravenous (i.v.) injections into the lateral tail vein of radioiodinated $^{125}$I-TNP- or $^{125}$I-lactosylated-St (most biodistribution experiments were done in the range of 1–10 μg protein, 1 mCi of $^{125}$I) into the lateral tail vein. At the time intervals indicated, blood samples were withdrawn from the tail, the mice were killed and their organs were dissected out, washed in PBS, blotted dry, weighed and counted for radioactivity. The results shown in Example 2, FIG. 2, are expressed as the average percentage of injected radioactivity dose per gram tissue (%/g ±SD) for pairs of CD-1 male mice. In subsequent experiments, CD-1 male mice were used and the results are presented as %/g or %/organ for single a single mouse or %/g ±SD or %/organ ±SD for pairs of mice unless otherwise stated.

EXAMPLE 1

TNP Modification and Radioiodination of Avidin, Streptavidin and BSA (i) TNP modification. TNBS dissolved in DDW (10 mg/ml) was reacted at a molar ratio of 200:1 with streptavidin, BSA, RNase, IgG and TABAD (1 mg/0.5 ml, 0.02M sodium bicarbonate) or at a molar ratio of 70:1 with avidin (extensive TNP substitution of avidin results in loss of avidin solubility). After 20 min at room temperature (RT), the pH was adjusted to 7.3 and the TNP proteins TNP-St, TNP-Av, TNP-BSA, TNP-RNase, TNP-IgG and TNP-TABAD were dialysed. FIG. 1 shows the substitution ratios TNP:St bound that were obtained under given reaction conditions (TNP:St added). The maximum expected ratio is 20:1.

(ii) Radioiodination. Proteins (0.2 mg/0.2ml) in 0.2M phosphate buffer pH 8.0 were reacted for 2 min with Na$^{125}$I (0.5 mCi for biodistribution experiment and 2.5mCi for external monitoring) in the presence of Chloramine-T (2mg/ml, 10 or 100 μl) in PBS for 2 min. The reaction, which facilitates attachment of the radioactive iodine to tyrosines, was terminated by the addition of sodium metabisulfite (2mg/ml, 10 or 100 μl) in PBS for 2 min followed by the addition of potassium iodide and carrier BSA (1 mg of each/0.1 ml PBS). The radioiodinated proteins $^{125}$I-TNP-proteins were then chromatographed on Sephadex G-25 in PBS. TNP modification can take place before or after radioiodination. Avidin and TNP-Av, being low in tyrosine content (molar ratio of 4 tyrosine/avidin as compared to 24 tyrosine/streptavidin), were radiolabeled by $^{125}$I-biotinyl-tyrosine as described below in Example 6.

EXAMPLE 2

Biodistribution Studies with $^{125}$I-TNP-St as Compared to $^{125}$I-TNP-BSA; Effect of dose and Exogenous Biotin In FIG. 2, monitoring of tissue from 14 h to 7 days showed a 33%/g retention in the liver at 14 h which increased to 42%/g at 24 h and slowly declined later on. Spleen levels were around 7–12%/g whereas levels at other tissues were low. The abbreviations used in this figure and in subsequent figures for tissues are as follows: H (heart); Lu (lung); Sp (spleen); Liv (liver); Kid (kidney); Bl (blood).

Figure 3A:
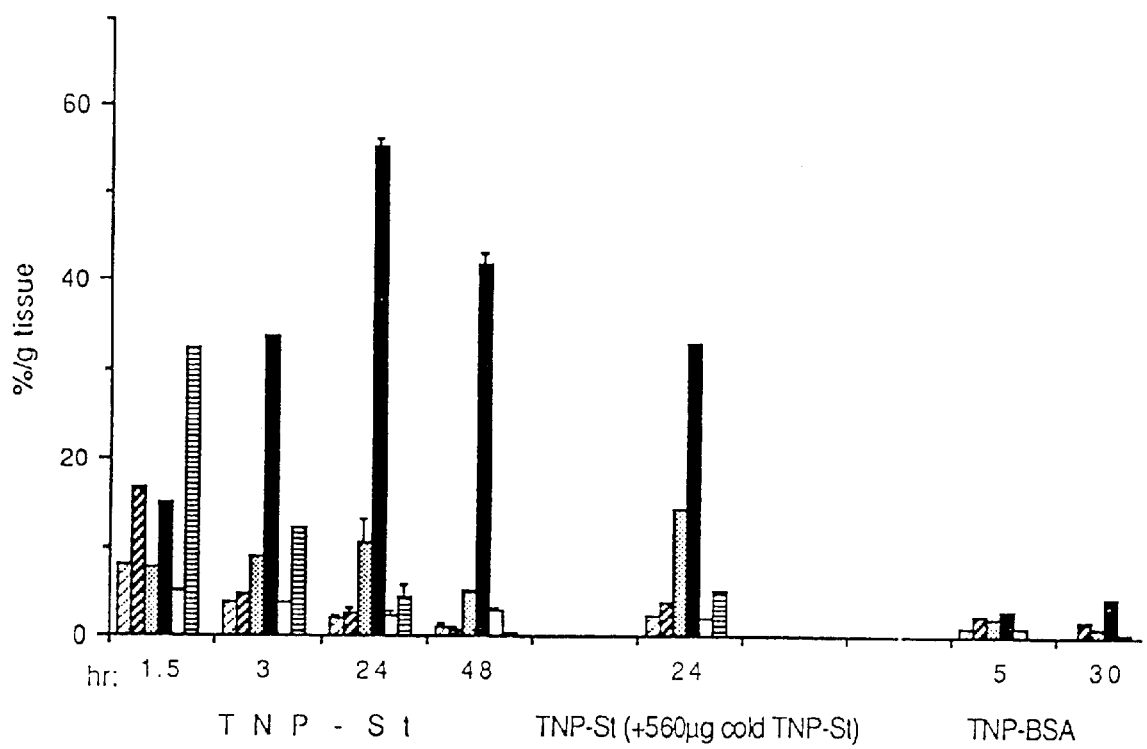
FIGS. 3A and 3B show the biodistribution in mice of $^{125}$I-TNP-St at 1.5–48 h at a low dose of 10 μg, the effect of addition of 560 μg non-radioactive TNP-St (to test for liver load) at 24 h, the biodistribution of $^{125}$I-TNP-BSA (FIG. 3A) and the effect of adding exogenous biotin on $^{125}$I-TNP-St accumulation (FIG. 3B), as described in Example 2.
Figure 3B:
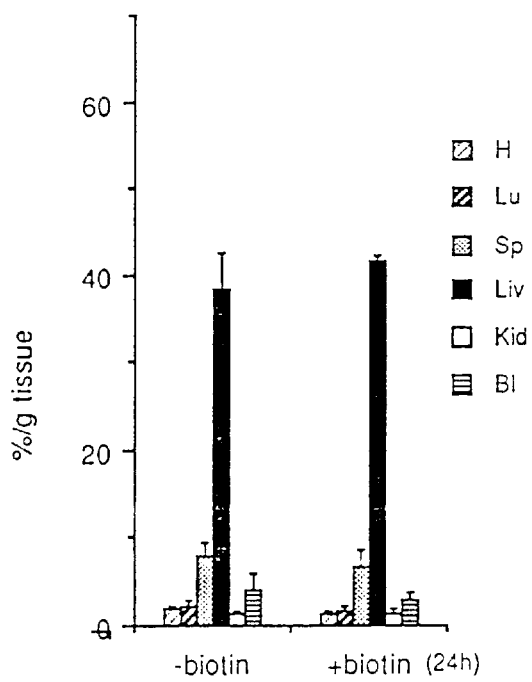

The biodistribution and tissue accumulation of $^{125}$-TNP-St (10 μg) was monitored at 1.5–48 h after i.v injection. As shown in FIG. 3A, accumulation of 15%/g was observed in the liver already at 1.5 h, although at this time high levels were found in blood and other organs. Liver accumulation increased to 35%/g at 3 h and was around 55%/g at 24 h while extrahepatic levels were low. Adding 560 μg non-radioactive TNP-St (cold TNP-St) to the 10 μg $^{125}$I-TNP-St reduced accumulation to 34%/g ((1−34/55)×100=38% of the 570 μg TNP-St could not be contained) at 24 h, i.e., liver capacity (load) for TNP-St under these conditions is around 350 μg. TNP-modification and radioiodination of a normally-cleared protein, such as BSA, did not alter its biodistribution pattern at 5 or 30 h. FIG. 3B shows that addition of exogenous biotin prior to injection did not alter the biodistribution pattern of $^{125}$I-TNP-St at 24 h.

EXAMPLE 3

Biodistribution at 2 h of Different Proteins Following TNP-Modification

Biodistribution of various TNP-proteins: TNP-BSA, TNP-IgG, TNP-RNase and TNP-TABAD, was studied 2 h after injection to CD-1 male mice.

Figure 4:
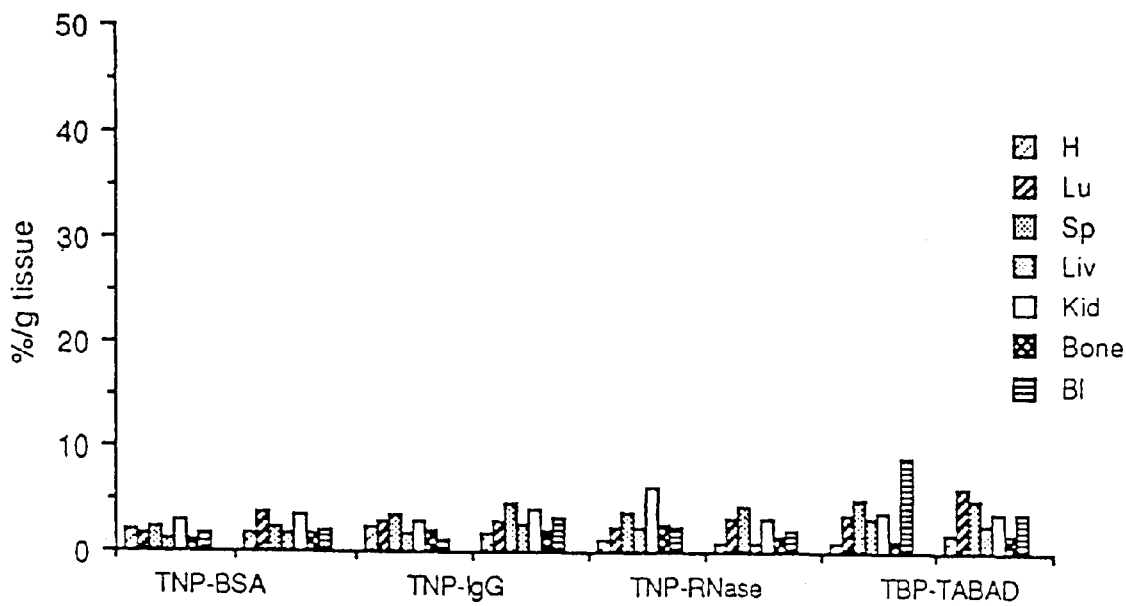
FIG. 4 shows the biodistribution in CD-1 male mice of several TNP-modified radioiodinated proteins (TNP-BSA, TNP-IgG, TNP-RNase and TNP-TABAD) at 2 h following injection, as described in Example 3.

As shown in FIG. 4, accumulation of these TNP-substituted proteins was found at low levels at 2 h indicating that generally TNP-modified proteins are rapidly cleared from the circulation and tissues, and that liver accumulation is a unique phenomenon characteristic to TNP-St and TNP-Av.

EXAMPLE 4

Biodistribution of $^{125}$I-TNP-St at Different TNP:St Molar Ratios

Samples of 1.5 nmol $^{125}$I-St in 0.2 ml 0.02M NaHCO$_3$ were reacted with 75, 150, 300 and 600μg TNBS/0.06 ml DDW for 30 min at room temperature. The samples were dialysed, measured for radioactivity and TNP-St molar substitution ratios were determined from the absorbance at 280 and 340 nm. CD-1 mice were injected i.v. with 20 μg/mouse of 125I-TNP-St (0.5–0.6×10$^6$ cpm) and 20 h later blood was withdrawn from the tail, the mice were killed, and their organs were dissected out, weighed and counted for radioactivity.

Figure 5:
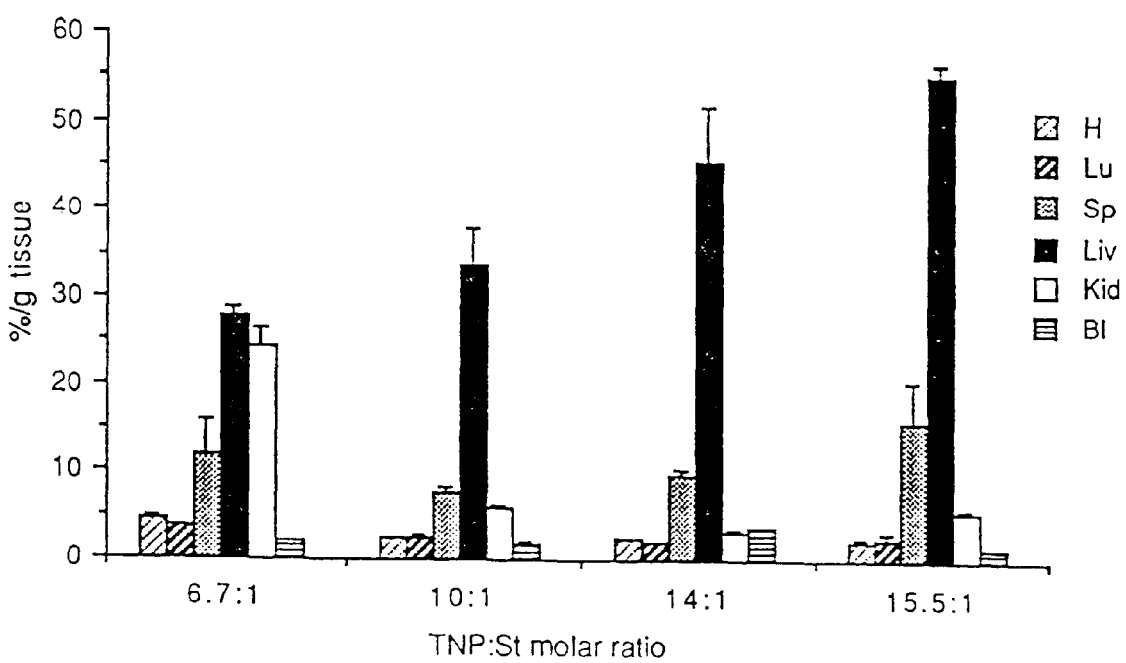
FIG. 5 shows the biodistribution in CD-1 male mice of $^{125}$I-TNP-St preparations at different TNP:St molar substitution ratios at 20 h, as described in Example 4.

The effect of TNP:St molar ratio on liver accumulation is illustrated in FIG. 5. TNBS was reacted with $^{125}$I-Streptavidin at different molar ratios, and TNP:St ratio (determination of A340 and A280 for TNP and protein, respectively) after dialysis showed a maximal ratio of 15.5:1 (max. expected=20:1). A low TNP:St ratio of 6.7:1 resulted in 24–27%/g accumulation in both liver and kidney. A ratio of 10:1 abolished kidney accumulation and increased liver accumulation to 34%/g. Ratios of 14:1 and 15.5:1 further increased liver accumulation values to 47 and 55%/g, respectively.

EXAMPLE 5

Figure 6A:
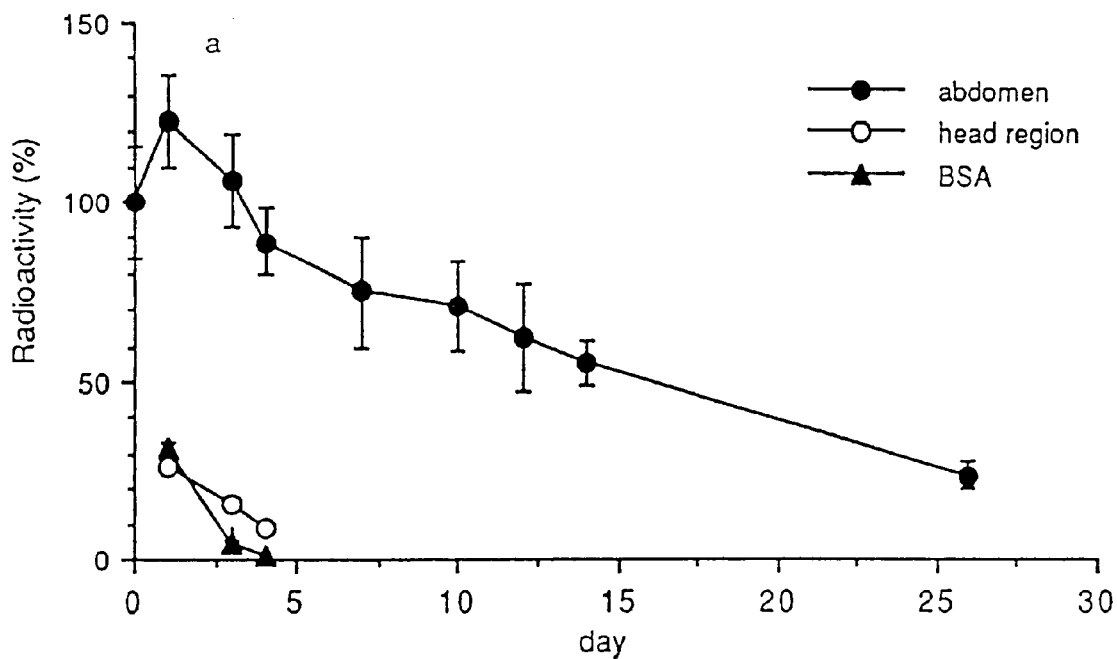
FIGS. 6A and 6B show the targeting of high dose 125I via TNP-St and the external monitoring of radioactivity at the liver and head regions of CD-1 athymic nude mice following injection of 0.16 mCi $^{125}$I-TNP-St or $^{125}$I-BSA (FIG. 6A) and the effect of said treatment on mice body weight (FIG. 6B), as described in Example 5.

Radioactive Monitoring at the Liver Region after Injecting Mice with $^{125}$I-TNP-St External Monitoring of Radioactivity. In experiments designed to evaluate the capacity of TNP-St to target high doses of 125I, athymic nude mice were injected i.p. with $^{125}$I-TNP-St (0.16 mCi/mouse). $^{125}$I-BSA was used as control. External radioactivity was monitored during a period of 26 days at the liver (right upper abdomen—lower chest) and at the head regions. The results are shown in FIG. 6A as the average percent of the decay in radioactivity in comparison to day-0 in groups of 5 mice.

Preliminary experiments to estimate the capacity of streptavidin to target to the liver therapeutic doses of radionuclides were performed in athymic nude mice which serve as carriers of human-derived tumors in pre-clinical experiments. $^{125}$I-TNP-St (0.16 mCi/mouse) was administered i.p. into CD-1 nude mice. Another group received $^{125}$I-BSA as control. As is illustrated in FIG. 6A, $^{125}$I radioactivity concentration in the liver region after 1 day was higher than when monitored on the day of injection (3 h post injection). Radioactivity declined slowly and still maintains high values of 55% on day 14 and 10% on day 26 (8 %/g tissue on day 26 by biodistribution analysis). Radioactivity at the head region declined to 30% already after one day and was observed to be 8% on day 4. In mice injected with $^{125}$I-BSA, radioactivity was down to 34% on day 1 and less than 1% on day 3.

Figure 6B:
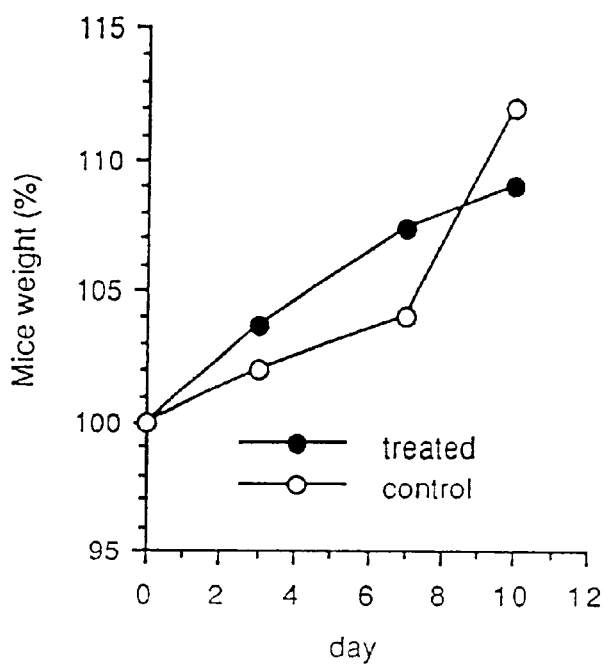
Figure 7A:
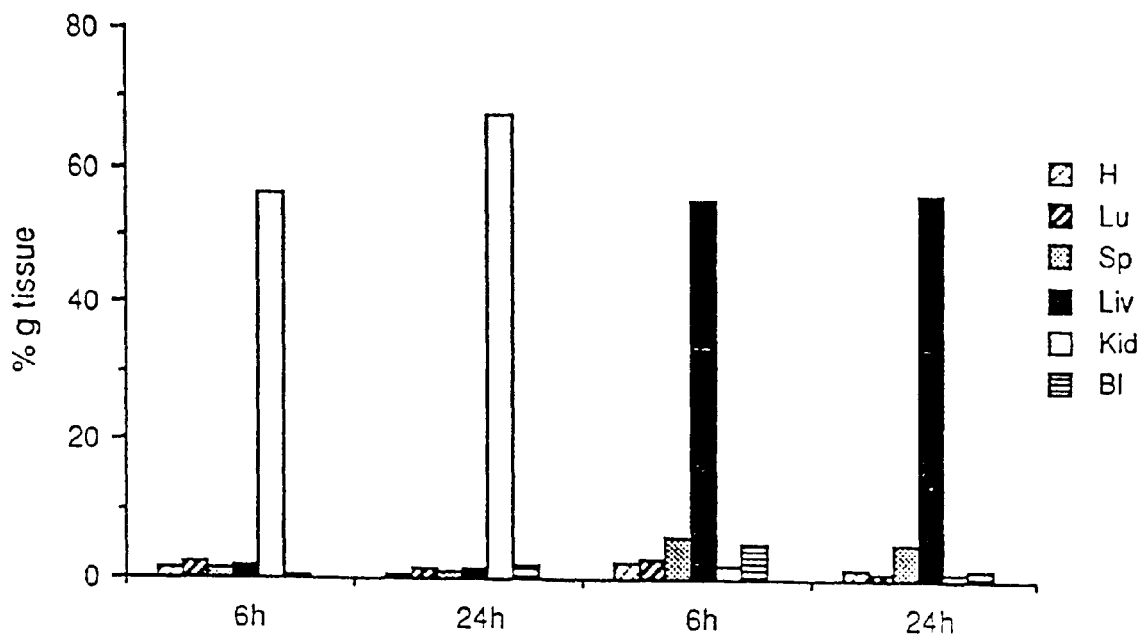
FIGS. 7A and 7B show accumulation in mice of $^{125}$I-BT complexed to St before and after TNP modification expressed in %/g tissue for biodistribution (FIG. 7A) or in % of injected dose/organ for organ accumulation (FIG. 7B), as described in Example 6.
Figure 7B:
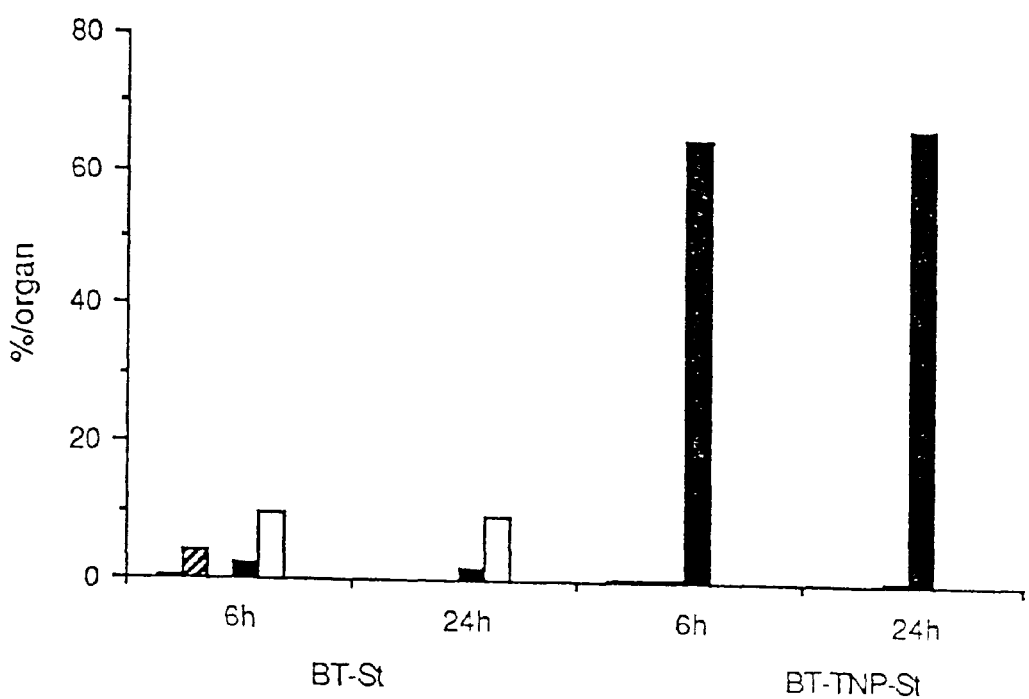
Figure 8A:
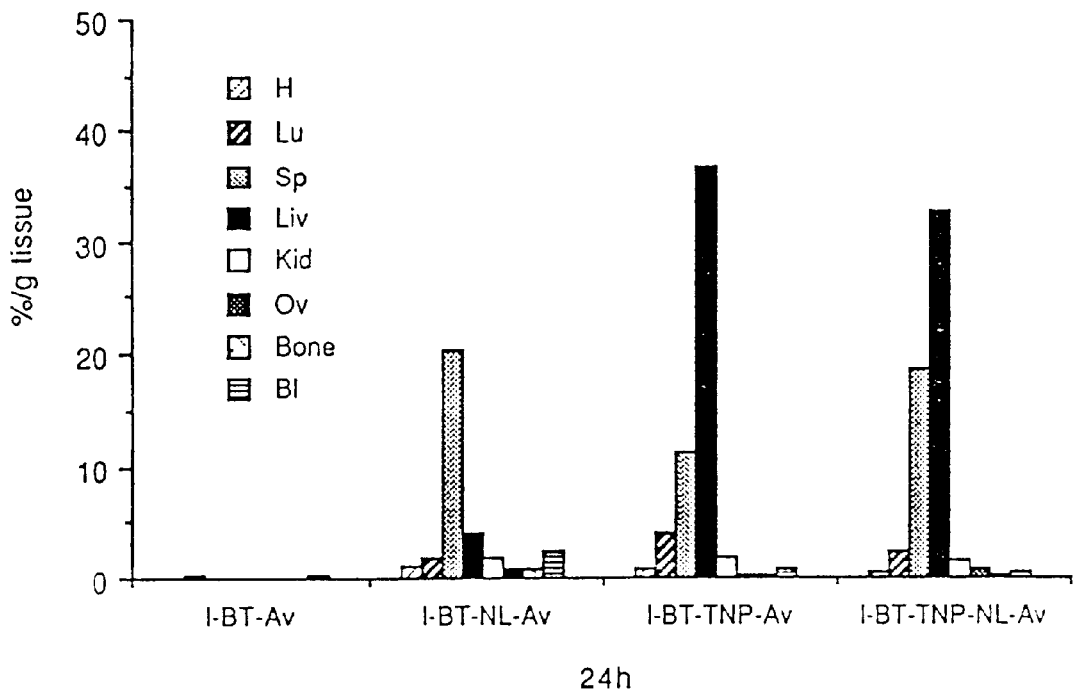
FIGS. 8A and 8B show biodistribution of $^{125}$I-BT complexed to Av or NL-Av before and after TNP modification at 24 h (FIG. 8A) and of 125I-BT-TNP-Av at 4 and 68 h (FIG. 8B), as described in Example 7.
Figure 8B:
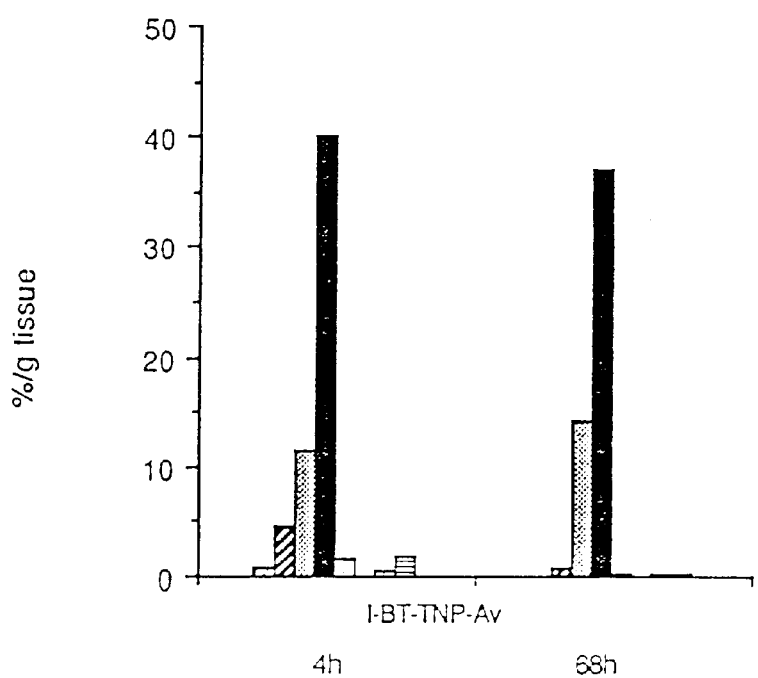
Figure 9:
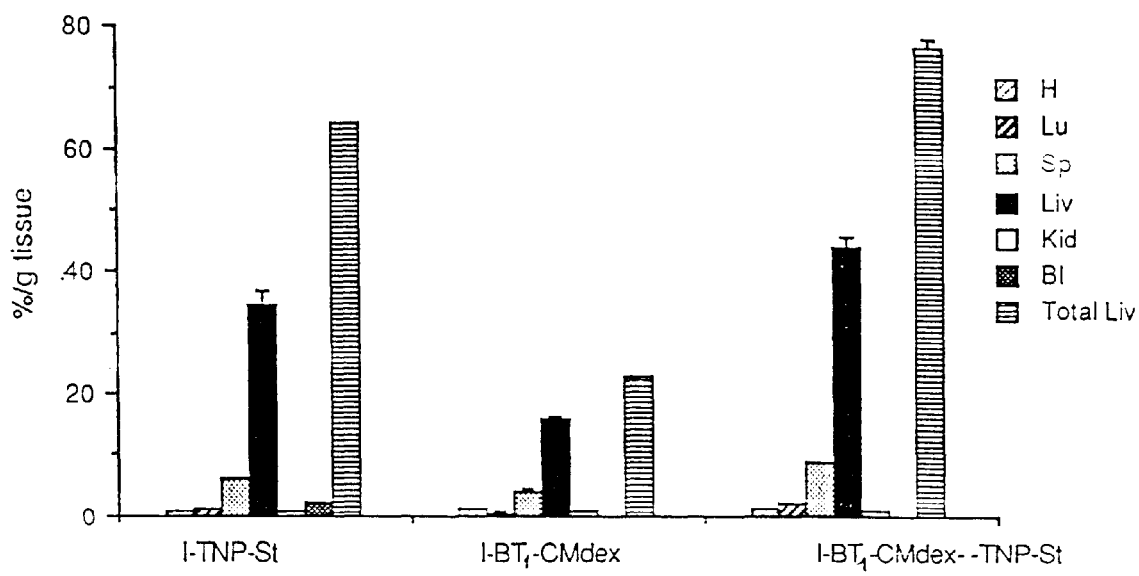
FIG. 9 shows targeting of $^{125}$I-BT$_1$-CMdex T-40 (Mr-40000) to the liver via TNP-St at 17 h in comparison to $^{125}$I-BT$_1$-CMdex or to $^{125}$I-TNP-St, as described in Example 8.

To examine the effect of the treatment on mice body weight, mice were weighed at the beginning of the experiment and at set time intervals thereafter. The results are expressed in FIG. 6B as % change in body weight for $^{125}$I-TNP-St-treated and control untreated mice (5/group). Mice body weight was not seen to be affected by the high and prolonged dose of $^{125}$I in the liver which indicates no major toxic manifestations by this treatment.

EXAMPLE 6

Targeting BT to the Liver Via TNP-St:
Biodistribution and Organ Accumulation of $^{125}$I-BT
Complexed to Non-Radiolabeled St before and after Its TNP Modification A low MW biotinylated ligand, namely, biotinyl-tyrosine, was used for targeting to the liver via TNP-St/Av. The tyrosine residues enabled radioiodination for the monitoring of biodistribution. Biotinyl-tyrosine (BT): Biotin-N-hydroxysuccinimide dissolved in DMF was reacted with 1.2 molar equivalence of tyrosine in DMF. After 24 h at RT, the DMF was evaporated and the BT was radioiodinated by the Chloramine-T method as described above in Example 1(ii). The radioiodinated BT was then reacted for 30 min with 0.2 mg of either streptavidin, avidin or their TNP derivatives at a molar ratio of 10:1 and the $^{125}$I-BT-proteins or $^{125}$I-BT-TNP-proteins were chromatographed on Sephadex G-25.

The targeting to the liver of radioiodinated biotinyl-tyrosine ($^{125}$I-BT) via TNP-St is shown in FIG. 7. CD-1 male mice were injected with 25 $\mu$g $^{125}$I-BT-St or $^{125}$I-BT-TNP-St and biodistribution was determined at 6 h and 24 h following injection. $^{125}$1I-BT complexed to unmodified streptavidin was retained in the kidney at levels of 58–68 %/g tissue (FIG. 7A). However, as with $^{125}$I-TNP-St, $^{125}$I-BT-TNP-St also accumulated in the liver, with 55–58%/g tissue at 6 h and 24 h following i.v. injection. The difference between the two organs is emphasized when organ rather than tissue accumulation is considered. In FIG. 7B, results are expressed as average % of injected dose of radioactivity/organ. It is shown that 66–68% of total $^{125}$I-BT-TNP-St accumulated in whole liver as compared to only 10% of $^{125}$I-BT-St accumulation in whole kidney.

EXAMPLE 7

Biodistribution of $^{125}$I-BT-Av or $^{125}$I-BT-NL-Av before and after TNP Modification at 24 h and Biodistribution of $^{125}$I-BT-TNP-Av at 4 h and 68 h Mice were injected i.v. with 50 $\mu$g $^{125}$I-BT-Av, $^{125}$I-BT-NL-Av, $^{125}$I-BT-TNP-Av or $^{125}$I-BT-TNP-NL-Av and biodistribution was determined at 24 h following injection.

As shown in FIG. 8A, no radioactivity was found in the tissues at 24 h following injection of $^{125}$I-BT-Av whereas $^{125}$I-BT-TNP-Av concentrated in the liver (40%/g vs. 12%/g in spleen and less than 4%/g in other tissues). Liver accumulation was also observed with TNP-BT-NL-Av: $^{125}$I-BT-NL-Av itself was cleared at a slower rate than $^{125}$I-BT-Av, with spleen values of 20%/g, but $^{125}$I-BT-TNP-NL-Av accumulated both in spleen (18/g) and liver (33%/g).

125I-BT-TNP-Av accumulation in the liver could be observed as early as 4 h and was still high at 68 h, as illustrated in FIG. 8B.

EXAMPLE 8

Targeting $^{125}$I-BT1-CMdex (T-10 and T-40) to the Liver

Biodistribution experiments showed that a high molecular weight biotinylated-ligand carrier, such as dextran T-40, can be targeted to the liver via TNP-St. Dextran or its derivatives have previously been shown to be extremely useful as intermediary carriers for drugs in immunotargeted systems (Schechter et al., 1991; Aboud-Pirak et al., 1989). In the present example, it is shown that complexing the dextran derivative $BT_1$-CMdex T-40 to TNP-St does not impair the liver accumulating property of TNP-St and therefore CMdex can be used as a drug carrier in this system.

For the preparation of biotinyl-diaminopropyl-tyrosyl-carboxymethyl dextran T-40 (BT1-CMdex T-40), DCC (1.14 g/10 ml dioxane) was added to a mixture of BOC-Tyr (1.37 g) and NHS (0.632 g) dissolved in dioxane (30 ml). After stirring overnight, dicyclohexylurea was filtered off, the BOC-Tyr-NHS was gradually added to a solution of diaminopropane (DAP) (4 ml/20 ml dioxane) and stirring proceeded for 12 h followed by filtration and vacuum evaporation of the filtrate. The concentrate was washed with cold ether, dissolved in minimal amount of methanol and precipitated with dichloromethane. BOC-Tyr-DAP (163 mg) was reacted with biotin-NHS (160 mg) in DMF, stirred for 3 h and the solvent was evaporated. The product was washed with cold water, dried and dissolved in methanol. Deprotection was carried out with trifluoroacetic acid (1 ml) and dichloromethane (1 ml) for 5 h followed by solvent evaporation, plaque-chromatography (in chloroform:methanol 3:1, Rf=0.67) and then harvesting the product biotinyl-DAP-tyrosine ($BT_1$).

CMdex T-10 or T-40 (prepared by carboxymethylation of dextran as previously described by Hurwitz et al., 1980) (40mg/ml) and $BT_1$ (3 mg) were dissolved in DDW and NHS (23 mg/0.2 ml) was added, followed by immediate addition of EDCI (150 mg/0.3 ml) while vortexing. The reaction mixture was stirred for 2–3 h at RT and the $BT_1$-CMdex was extensively dialyzed against DDW. The product contained 2–3 mol $BT_1$/mol CMdex as determined by tyrosine absorption at 280 nm or by a biotin assay (Schechter et al., 1991). Following radioiodination, the $^{125}$I-$BT_1$-CMdex T-40 preparation was reacted with TNP-St at a molar ratio of 4:1 for liver targeting.

CD-1 male mice were injected i.v. with either 1 $\mu$g TNP-St complexed to $^{125}$I-$BT_1$-CMdex T-40 (1:4 molar ratio), $^{125}$I-$BT_1$-CMdex T-40 alone or $^{125}$I-TNP-St, and 17 h later biodistribution was determined. As shown in FIG. 9, low accumulation of $^{125}$I-$BT_1$-CMdex T-40 itself in the liver was observed (16%/g). However, upon complexing with TNP-St, its accumulation increased to 45%/g as compared to $^{125}$I-TNP-St (35%/g). Total liver accumulation values for $^{125}$I-$BT_1$-CMdex, $^{125}$I-TNP-St and $^{125}$I-$BT_1$-CMdex-TNP- St were 22, 65 and 78%, respectively (%/organ values are more reproducible than %/g tissue, the last being affected by total tissue weight). Similar results were obtained with $^{125}$I-BT$_1$-CMdex T-10: here the contribution to accumulation of the $^{125}$I-BT$_1$-CMdex was even smaller (10/g). $^{125}$I-BT$_1$-CMdex can be targeted to the liver also via TNP-Av (data not shown); in fact its complexing to TNP-Av supported TNP-Av solubility and thus enabled increased TNP substitution. This phenomenon is of great importance since avidin is far more available and less costly than streptavidin.

EXAMPLE 9

Targeting to the Liver $^{125}$I-BT$_1$-CMdex-5-Fluorouridine (FUR) via TNP-St or TNP-Av: Monitoring Carrier Radioactivity The present inventors have previously studied immuno-targeting of chemotherapeutic drugs, such as CDDP, daunomycin, adriamycine and 5-fluorouracil (5FU), and for this purpose developed drug-carrier-antibody conjugates with emphasis on the preservation of the pharmacological activity of the drug (Schechter et al., 1986b; Schechter et al., 1987a; Schechter et al., 1989b; Arnon et al., 1989).

CMdex-hydrazine was found to be an appropriate carrier for the chemotherapeutic drug 5-fluorouridine (FUR). Previous studies showed that the pharmacological activity of CMdex-NH$_2$-FUR was preserved due to non-reduced Schiff bases formed between the oxidized FUR and NH$_2$ of hydrazine (Hurwitz et al., 1985).

BT$_1$-CMdex T-40 was used as an intermediary carrier in targeting FUR to the liver using TNP-St/Av as a vehicle. Oxidized FUR was attached to hydrazide residues coupled to carboxyl groups of BT$_1$-CMdex as previously described (Hurwitz et al., 1985). The BT$_1$-CMdex-FUR contained 27 FUR/CMdex as determined by the TNBS assay for hydrazides (Miron et al., 1976) before or after FUR coupling. The product was radioiodinated and reacted with TNP-St or TNP-Av at a molar ratio of 4:1 and an assay for biotin binding sites (Schechter et al., 1991) indicated complete occupancy of these sites by the biotinyl groups of BT$_1$-CMdex-FUR.

Figure 10:
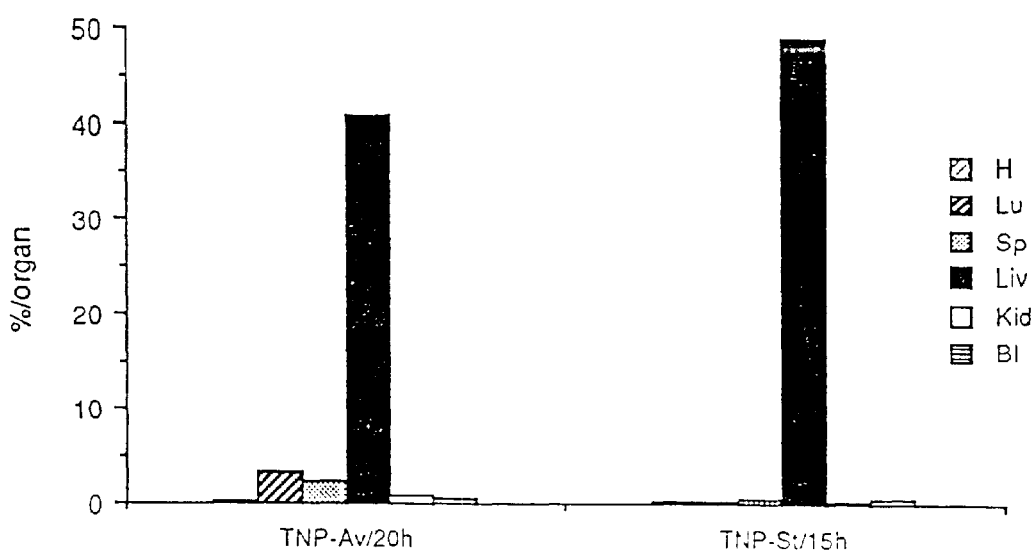
FIG. 10 shows liver targeting of $^{125}$I-BT$_1$-CMdex-FUR via TNP-AV or TNP-St, as described in Example 9.

CD-1 mice were injected i.v. with either TNP-St or TNP-Av complexed to $^{125}$I-BT$_1$-CMdex-FUR. As shown in FIG. 10, targeting of $^{125}$I-BT$_1$-CMdex-FUR to the liver could be demonstrated by monitoring $^{125}$I-radioactivity of the FUR-carrier at 20 h for TNP-Av and at 15 h for TNP-St.

EXAMPLE 10

Figure 11A:
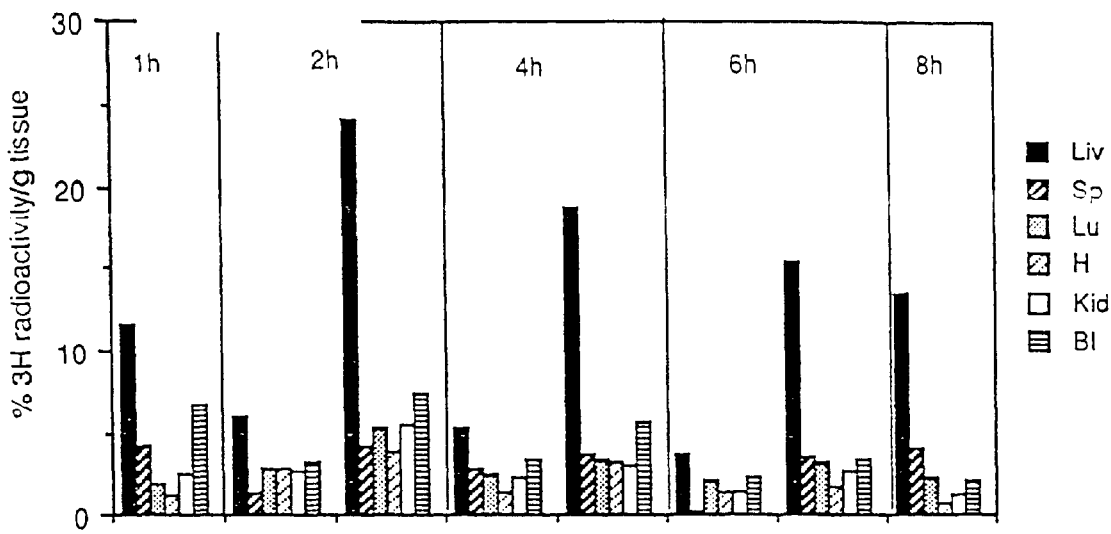
FIGS. 11A and 11B show biodistribution (FIG. 11A) and organ accumulation (FIG. 11B) of FUR (trace labeled with $^3$H-uridine) targeted to the liver following its coupling to BT$_1$-CMdex-hydrazide and complexing the BT$_1$-CMdex-FUR product to TNP-St prior to injection, as compared to uncomplexed BT$_1$-CMdex-FUR. [$^3$H] radioactivity in tissue extracts was measured at 1, 2, 4, 6 and 8 h after injection and the results are expressed in %/g tissue (FIG. 11A) or %/organ (FIG. 11B), as described in Example 10.
Figure 11B:
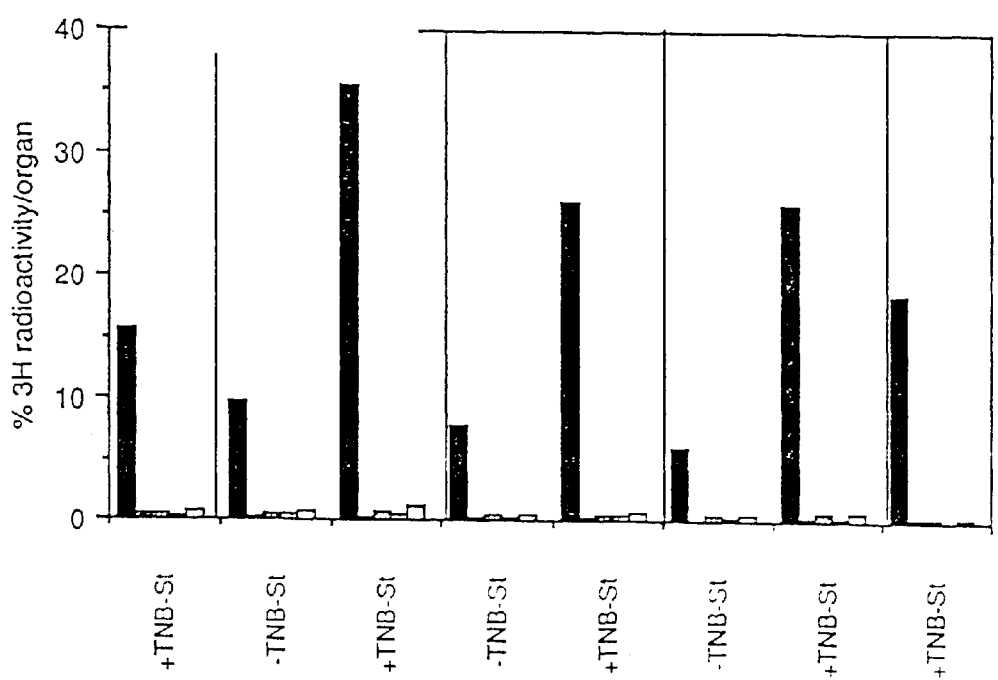

Targeting to the Liver of FUR (Trace Labeled with [$^3$H]-uridine) Attached to BT1-CMdex-TNP-St: Monitoring [$^3$H] Radioactivity The actual targeting of FUR to the liver was carried out by a BT$_1$-CMdex (T-40)-FUR product in which FUR was trace-labeled with [$^3$H] uridine. Mice were injected with BT$_1$-CMdex-FUR-([$^3$H]-uridine) alone or complexed to TNP-St and at set time intervals blood was withdrawn, organs were dissected out and weighed. Tissue extracts were prepared by blending blood and organs in an Ika Werk Ultra-Turrax blender in 5× vol (ml)/tissue weight (g) of 0.1N NaOH for 30 sec. After centrifugation, 50 μl samples were counted for [$^3$H] radioactivity. Results are expressed as %/g tissue or %/organ. As shown in FIGS. 11A and 11B, levels of untargeted BT1-CMdex-FUR ([$^3$H]-uridine) were low. However, clear accumulation of the drug was observed in the liver when targeted via TNP-St: Accumulation of 12%/g was observed at 1 h, 24%/g at 2 h (37%/liver) which later on slowly declined to 13%/g at 8 h (FIG. 11A). Radioactivity levels in other organs were in the range of 5%/g tissue or less than 1%/organ (FIG. 11B). It can be calculated that upon injection of 200μg TNP-St as a vehicle for BT1-CMdex-FUR, 25 μg of the drug can be accumulated per gram liver. Injection of free FUR+([$^3$H]-uridine) resulted in its rapid clearance and low levels around 1%/g tissue were monitored at 1 and 4 h.

EXAMPLE 11

Targeting to the liver of CDDP complexed to BT$_1$-CMdex-TNP-St

CMdex was found to be an appropriate carrier for CDDP since complexes between CDDP and CMdex are pharmacologically active due to the ability of the drug to dissociate from the carrier in favor of ligands exhibiting higher affinity towards the Pt drug (CDDP), such as DNA, which is the target for CDDP activity in tumor cells. Pharmacokinetic studies confirmed the assumption of sustained release and prolonged maintenance of the complexed drug, as compared to the rapid elimination and inactivation of the free drug (Schechter et al., 1989a). Complexing CDDP to BT$_1$-CMdex: BT$_1$-CMdex (T-40) (0.15mM) was reacted with CDDP in DDW at a molar ratio of 1:60 for 24 h at 37° C. Following dialysis, the resulting BT$_1$-CMdex-Pt contained 23–27 CDDP/CMdex. The complex BT$_1$-CMdex-CDDP was reacted with TNP-St (at a ratio of 4:1) for targeting to the liver. CDDP complexing to BT$_1$-CMdex did not affect BT$_1$-CMdex targeting to the liver via TNP-St or TNP-Av, as demonstrated by using $^{125}$I-labeled carrier. To show the actual targeting of CDDP to the liver, CDDP was quantitatively determined in organs obtained at set time intervals following injection of 185 μg CDDP complexed to BT$_1$-CMdex-TNP-St. Blood and organs were blended in an Ika Werk Ultra-Turrax blender (Jankel&Kunkel KG) in 5×Vol/tissue weight of 0.1N NaOH for 30 seconds. After centrifugation, the supernatants were filtered through Minisart 5 μm filter and the Pt content in the samples was determined by flame atomic absorption spectrometry (AA) at 265.9 nm in air-acetylene flame (in a Perkin Elmer 5100 PC spectrophotometer). Standards were prepared in a solution with matrix identical to that of the samples (i.e., normal tissues), to account for possible matrix interference. Results are expressed as %/g, i/organ or μg/organ in individual mice.

Figures 12A, 12B:
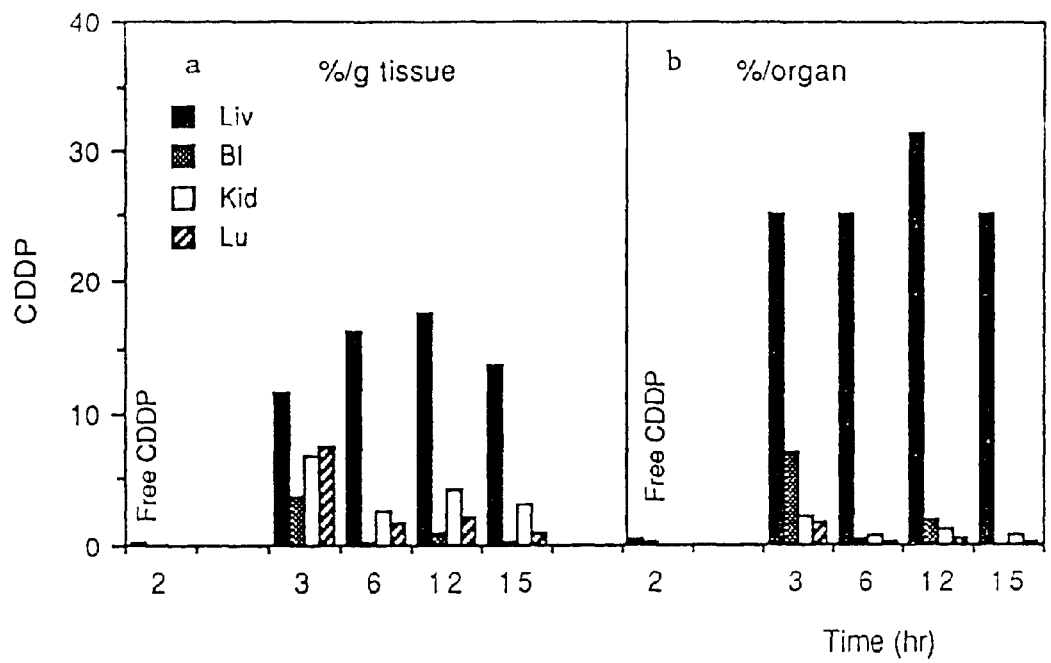
FIGS. 12A–C show targeting of CDDP to the liver following its complexing to BT$_1$-CMdex and reacting the complex with TNP-St prior to injection. The Pt metal in tissue extracts was monitored by atomic absorption spectrometry at 3, 6, 12 and 15 h as compared to monitoring at 2 h following injection of free CDDP (300 μg). The results are expressed as %/g tissue (FIG. 12A), %/organ (FIG. 12B) or μg/organ (FIG. 12C), as described in Example 11.
Figure 12C:
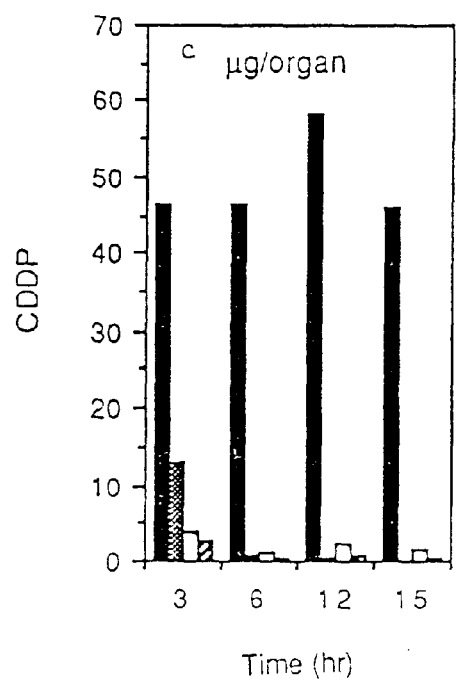

As shown in FIG. 12A, AA measurements showed clear accumulation of the Pt drug in the liver: administration of 185pg complexed (targeted) CDDP resulted in 11.5%/g liver accumulation at 3 h which increased to 17.7%/g at 12 h and later declined to 13.8%/g at 15 h. Accumulation in other organs tested was low. Liver accumulation of CDDP was emphasized when organ content was considered: 25–31%. of the injected dose (47–57 μg) was found in whole liver (FIGS. 12B and 12C). Quantitative determination of CDDP in organs obtained at 2 h following injection of 300 μg free CDDP showed that essentially no Pt could be found in liver or other organs.

EXAMPLE 12

Gd Liver Targeting Via Biotinyl-DTPA-(Lys)$_{19}$ Complexed to TNP-St

Figure 13:
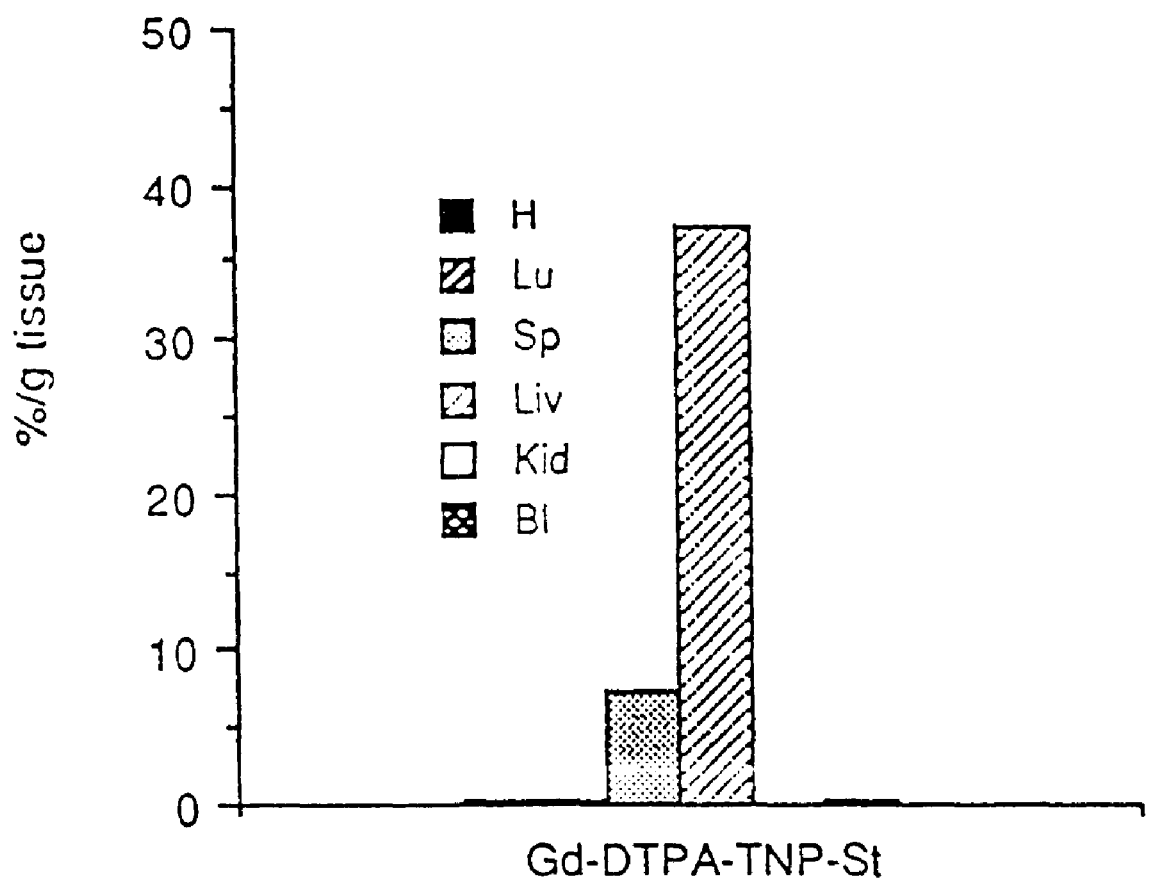
FIG. 13 shows targeting to and accumulation in the liver at 15 h of Gd-DTPA-biotinyl-(Lys)$_{19}$ complexed to $^{125}$I-TNP-St at a ratio of 4:1, as described in Example 12.

Another type of carrier which was tested for its ability to be targeted to the liver via TNP-St was poly-L-lysine. The importance of poly-L-lysine is that: (a) it can serve as a carrier for a large variety of ligands due to its high content of NH$_2$ groups; (b) it may be useful in gene targeting since poly-L-lysine forms strong, non-damaging electrostatic interactions with DNA thus generating a soluble complex that enables gene targeting to liver cells when linked to TNP-St/Av; and (c) it can be modified with DTPA or other chelate groups for use in carrying radionuclides or MRI reagents, such as Gd (Hurwitz et al., 1985). Preliminary experiments were performed with biotinyl-(Lys)$_{19}$-DTPA-Gd which was complexed to $^{125}$I-TNP-St. B-(Lys)$_{19}$-DTPA-Gd-$^{125}$I-TNP-St: Biotin-N-hydroxysuccinimide was reacted with (Lys)$_{19}$ at a ratio of 0.8 mol biotin:1 mol polymer. The biotinyl-(Lys)$_{19}$ (3.7 mg/5ml of 0.1M Hepes buffer pH 8.8) was reacted with the cyclic anhydride of DTPA (100 mg/0.3 ml DMSO) and the pH was adjusted to 8.5 with 3N NaOH. After 2 hr at 40° C., streptavidin (3 mg/0.3 ml PBS) was added for 2 h and the complex was dialysed against citrate buffer 0.1M pH 6.5. GdCl$_3$ (6 mg/0.5 ml 0.1M acetate buffer pH 6.0) was then reacted with the DTPA-B-(Lys)$_{19}$-St for 24 h at 40° C. and the product Gd-(DTPA-B-Lys)$_{19}$-St (hereinafter Gd-Lys-St) was chromatographed on Sephadex G-50. NMR analysis of the preparation showed that the molar ratio of Gd:St was 50:1. The streptavidin of Gd-Lys-St was radioiodinated with 125I and modified with TNBS as described above. The Gd-DTPA-Lys-TNP-St was injected into a CD-1 mouse and biodistribution determined 15 h later (FIG. 13). The resulting complex accumulated in the liver at 35%/g. The capacity of TNP-St and TNP-Av to target Gd to the liver thus provide an important vehicle for MRI imaging procedures.

EXAMPLE 13

Toxicity Studies

The histological patterns of sections from livers obtained from CD-1 mice at 4, 8, 12, 16 and 24 days following injection of 200 μg TNP-St were the same as of normal tissues, i.e., no pathological changes were observed. Injecting mice with a dose of 300 μg TNP-St, TNP-Av and their BT$_1$-CMdex complexes did not seem to affect their body weight or survival (observed for 4 months).

EXAMPLE 14

Trinitrophenyl (TNP) as a Kupffer Cell Trafficking Marker

The specific and long-term accumulation of TNP-modified stretpavidin and avidin in Kupffer cells is believed to be attributed to two parameters: (a) the increased uptake due to the TNP marker; and (b) the unusual resistance of streptavidin and avidin to proteolytic enzymes. This assumption could be verified by testing normally-degraded proteins that were modified with TNP. The laboratory of the present inventors have observed that TNP modified proteins, such as BSA, ovalbumin (Ov) or RNase, did not accumulate in the liver or in any other organ when monitored at 2,3,5 or 24 h after administration. This could be due to rapid uptake, degradation and clearance so that the possibility of earlier accumulation could not be excluded. In this example, the disposition profiles of such TNP-proteins were evaluated at shorter time intervals following administration.

Figure 14A:
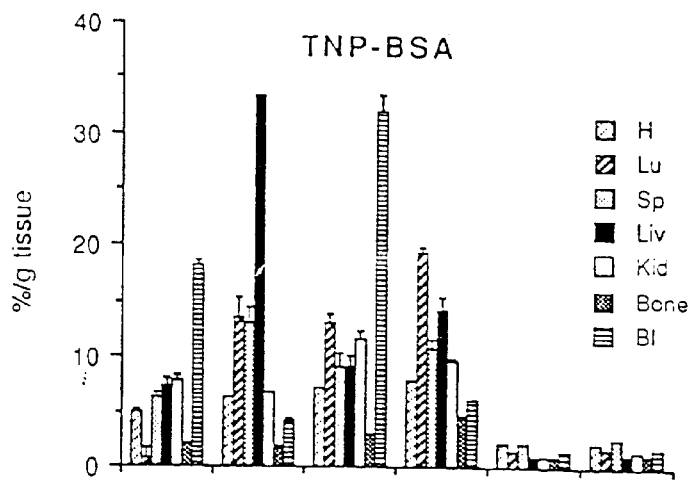
FIGS. 14A–C show biodistribution of radioiodinated BSA (FIG. 14A), Ov (FIG. 14B) and St (FIG. 14C) with and without TNP modification in CD-1 mice at 15–180 min following i.v. injection. Results of all experiments are expressed as mean %/g tissue ±SD for pair of CD-1 male mice.
Figure 14B:
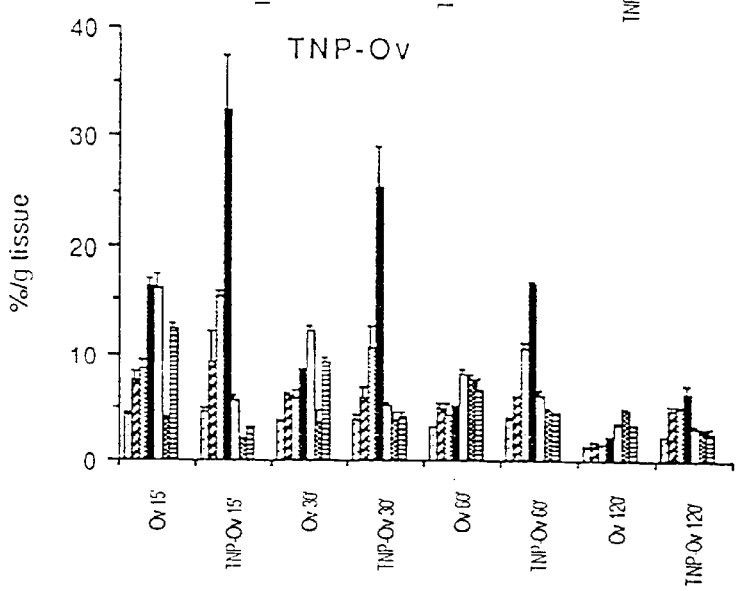
Figure 14C:
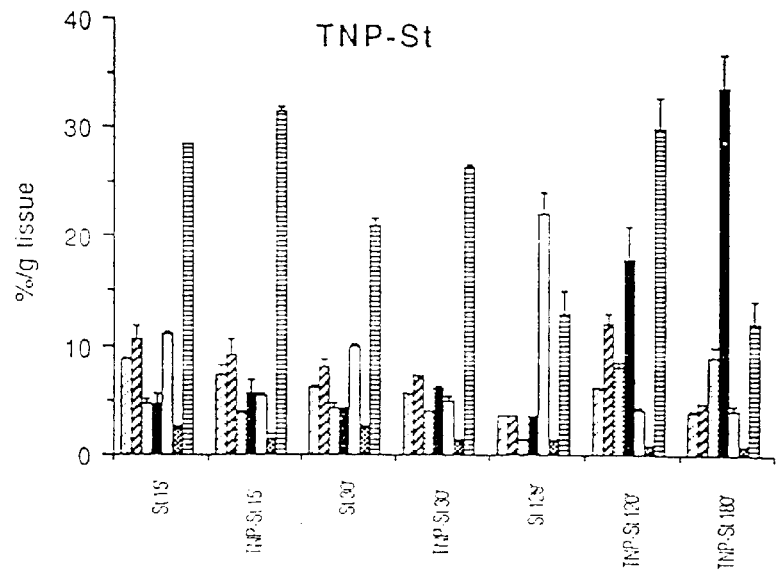

When tested at a time range of 15–120 min, TNP modification of BSA and Ov led to rapid hepatic uptake as compared to the unmodified proteins. At 15 min, TNP-BSA levels were higher in liver (34%/g) and spleen (13%/g) but lower in blood (3%/g) as compared to unmodified BSA (8%/g in liver, 7%/g in spleen and 28%/g in blood) (FIG. 14A). At the 30 min. timepoint, liver values of TNP-BSA declined to 24%/g, and at two hours (2 h), BSA and TNP-BSA were down to <3%/g in blood and organs. Similar results were obtained with Ov (FIG. 14B), although in this case clearance was somewhat slower (33%, 25% and 17%/g liver at 15, 30 and 60 min, respectively). At the two hour timepoint, both TNP-Ov and Ov were down to <6%/g. The biodistribution profile of TNP-St was different (FIG. 14C): blood levels for both TNP-St and St were kept high for a longer period of time (22–33%/g) whereas levels in other tissues, including the liver, were low (<10%/g). Elevation of St in the kidney and TNP-St in the liver was delayed and started to build up at 2 h (23% and 18%/g, respectively). These results indicate that TNP-modification of proteins increases their uptake by the liver. The slow degradation and processing of St and TNP-St leads to retardation of uptake and to subsequent accumulation in the target organs.

Figure 15:
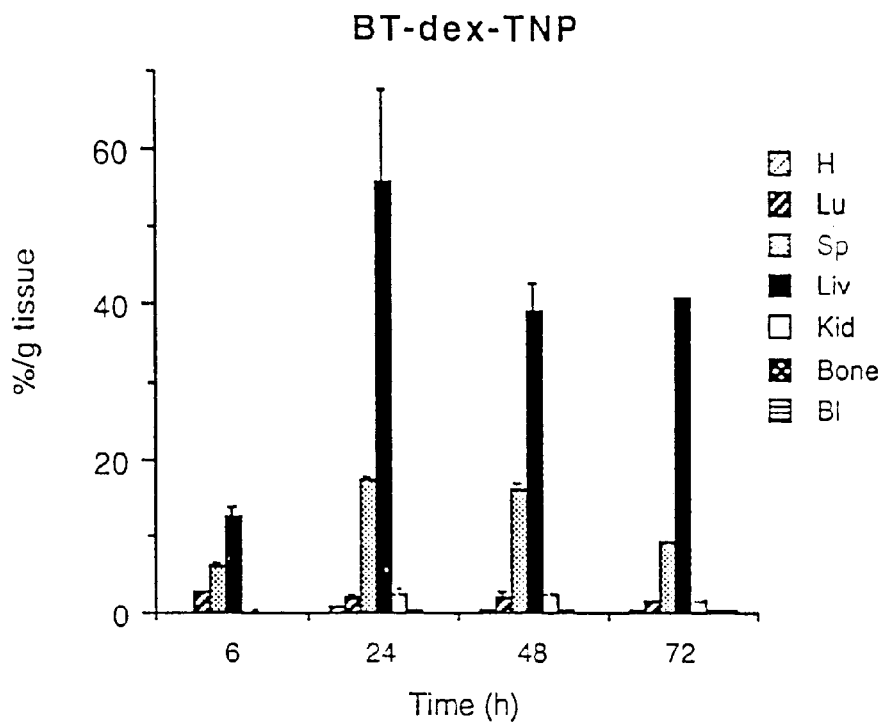
FIG. 15 shows the biodistribution in mice of radioiodinated BT-dex-TNP.

According to this scheme, any combination between an enzyme resistant macromolecule and TNP is bound to exhibit a disposition profile similar to that of TNP-St. To verify this assumption, another non-biodegradable macromolecule, i.e., a dextran derivative (CMdex, 40 kDa) was tested. Biotinyl-tyrosyl-CMdex (BT-dex, tyrosyl served for iodination; the biotinyl residue was non-functional in this case) was reacted with hydrazine and the BT-dex-hydrazide formed was modified with TNBS to produce BT-dex-TNP. The biodistribution profile of the radioiodinated product (FIG. 15) showed a gradual and prolonged accumulation in the liver with 11%/g at 6 h, 55%/g at 24 h and 38%/g at 48 and 72 h.

Figure 16:
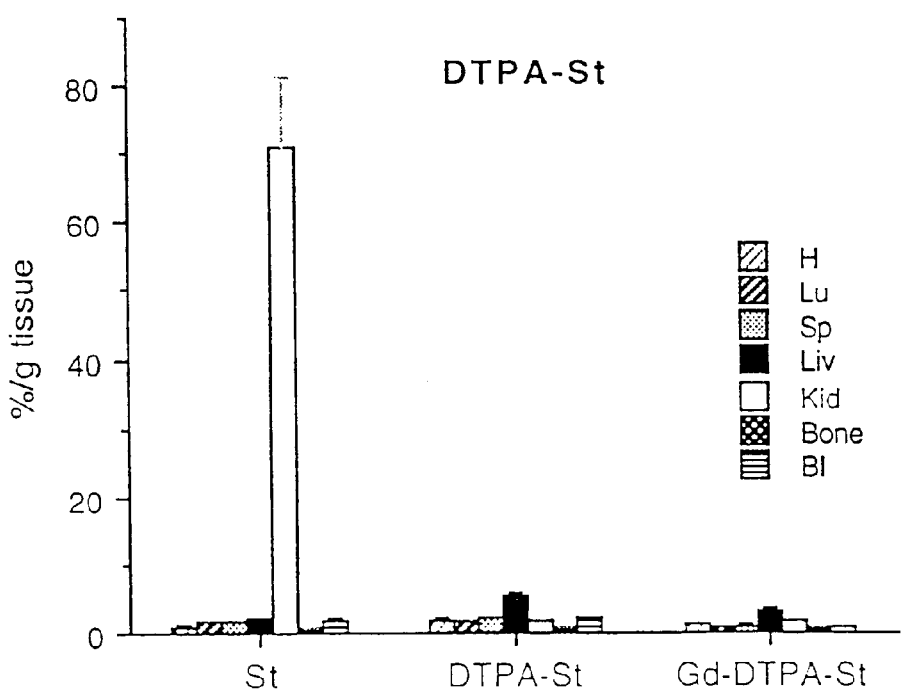
FIG. 16 shows the biodistribution in mice of radioiodinated St and its DTPA or Gd-DTPA derivatives at 24 h.

Hepatic uptake may also depend on charge. For instance, the relative contribution of nonparenchymal cell uptake was shown to be correlated with strongly anionic molecular forms. Smedsrod (1990) reported that liver uptake can be mediated by avid binding of scavenger receptors on macrophages and endothelial cells to negatively charged reagents and followed by receptor mediated endocytosis. Streptavidin is a neutral protein (contains 16 Asp, 16 Glu, 20 Lys and 12 Arg) and TNP modification could produce a negatively charged protein since substitution neutralizes the positive charge of the ε-amino group of lysine. Although a marked increase in the anionic charge of the molecule is not expected (Arg is not substituted), whether another type of lysine substitution may lead to liver accumulation of streptavidin was also tested. Streptavidin was reacted with diethylenetriamine-pentaacetic acid (DTPA) anhydride, a chelating ligand used as a carrier for metal ions (e.g., gadolinium -Gd). DTPA not only neutralizes ε-amine/lysine but also adds another carboxyl group, thus contributing to the net negative charge. DTPA or DTPA-Gd substituted St did not accumulate in the liver, and kidney accumulation was completely abolished (FIG. 16). This indicates that lysine-substituted streptavidin has little or no interaction with liver sinusoidal or Kupffer cells having scavenger receptors for polyanionic macromolecules. Thus, it is believed that uptake of TNP-modified macromolecules by Kupffer cells could be due to a specific fluid-phase or adsorptive endocytosis-pinocytosis, or hydrophobic epitopes like TNP to specific receptor-mediated endocytosis.

EXAMPLE 15

Targeting to Liver Hepatocytes Via the Lactose Marker

The effect of chemically modified streptavidin with lactosyl groups on its in vivo distribution was studied in mice.

This was done by covalent attachment of reducing carbohydrates to the protein via reductive amination with cyanoborohydride anion (Schwartz, 1977). Lactosylation of proteins through ε-amino (NH$_2$) groups of lysine residues by reductive deamination with cyanoborohydride was performed according to Gray (1974). Streptavidin, avidin or BSA (3 mg/0.1 ml 0.2M potassium phosphate pH 8.0), lactose (5 mg/0.1 ml of the same buffer) and sodium cyanoborohydride (5 mg/0.1 l of the same buffer) were mixed and incubated for 5 days at 37° C. Following extensive dialysis, the molar substitution ratio of the lactosyl-protein derivatives was analyzed as follows: a lactosyl-protein sample in 0.8 ml DDW was mixed with 0.5 ml 5% phenol and 2 ml concentrated sulfuric acid. The lactose content was determined from the absorbance at 485 nm in comparison to a standard concentration curve of lactose and after subtracting background levels of the unmodified proteins. Protein concentration was determined from absorbance at 280 nm. The molar substitution ratios for streptavidin, avidin and BSA were 5:1, 8.1:1 and 8.6:1 lactose/protein, respectively.

Reductive amination is a lengthy process, and in order to achieve higher substitution ratios, a modification to the method was introduced by which a large batch of lysine (68 mg) is subjected to a prolonged reductive amination (37 days at 37° C. under sterile conditions) in the presence of lactose (2800 mg) and sodium cyanoborohydride (480 mg), all dissolved in 6 ml of 0.2M potassium phosphate pH 8.0. The mono- or di-lactosyl-lysine is then used for conjugation through its carboxyl group to ε-amino groups of lysine residues in proteins as follows: protein (1 mg) and lactosyl-lysine (0.5 mg) in 0.3 ml DDW were mixed with N-hydroxysuccinimide (NHS) (0.2 mg) and then immediately with 1-ethyl-3 (3-dimethylaminopropyl)-carbodimine (EDCI) (2 mg) while vortexing. The reaction proceeded for 4 hr at room temperature and then dialysed extensively against DDW. The molar substitution ratios for lactosyl-lysyl-(Lac-Lys) modified streptavidin, avidin and BSA were 13.3:1, 19:1 and 8.4:1 lactose/protein, respectively. Biodistribution of the above preparations showed low liver accumulation of Lac-Lys-BSA (17%/g at 15 min that declined already at 30 min), short-term liver accumulation of Lac-Lys-Av (28% at 15 and 30 min which declined to 16%/g already at 1 hr) and high and prolonged liver accumulation by Lac-Lys-St (20–30%/g, or 35–48%/liver, from 15 min to 48 hr and still 22%/g at 72 hr).

Figure 17A:
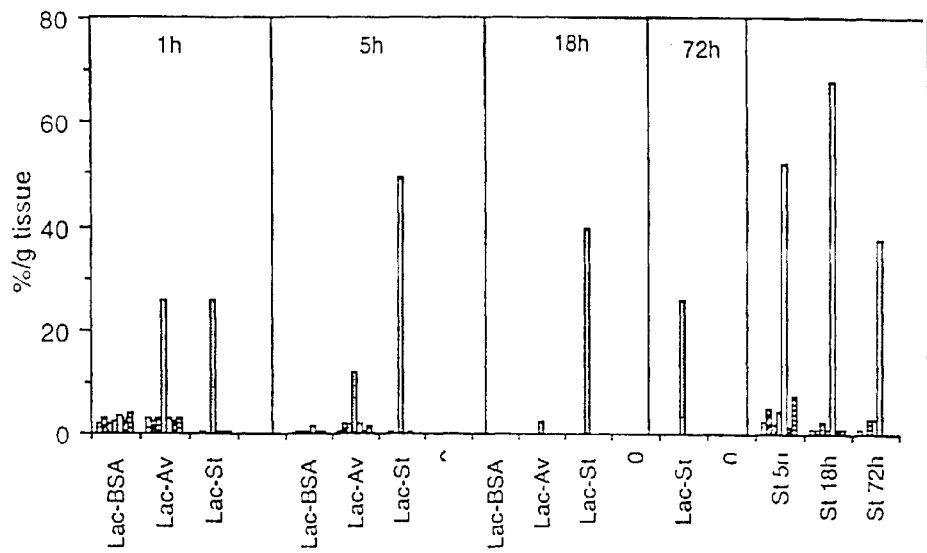
FIG. 17A shows the biodistribution of lactosylated derivatives of BSA, Av and St (molar substitution ratios of 8.6:1, 8.1:1 and 5:1, respectively) and accumulation of Lac-St in comparison to St alone.
Figure 17B:
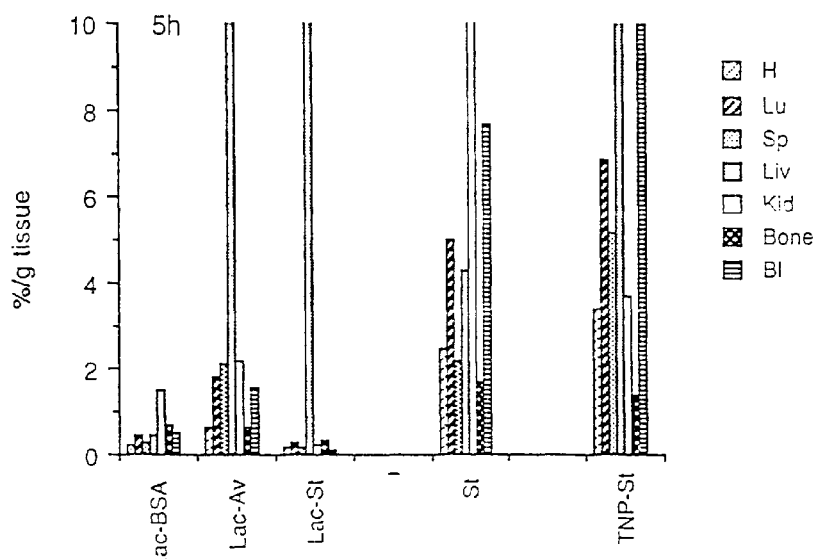
FIGS. 17B and 17C show the biodistribution of lactosylated BSA, Av and St in comparison to St and TNP-St at 5 h—Liver accumulation (left) and tissue distribution (right).
Figure 17C:
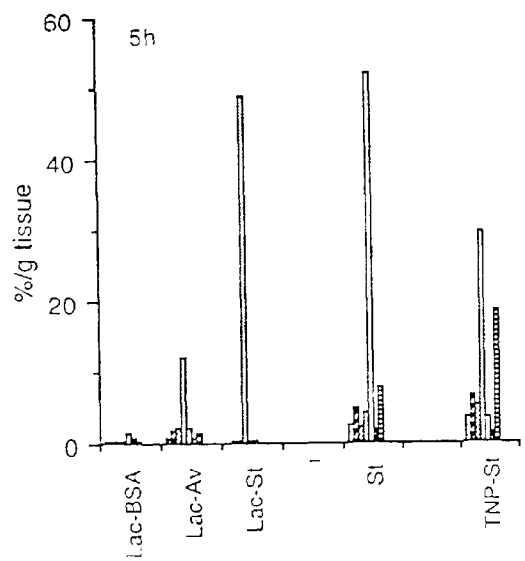

Biodistribution studies were also performed with lactosyl (Lac)-St, Lac-Av and Lac-BSA at molar substitution ratios of 5:1, 8:1 and 8.6:1, respectively. Mild lactosylation of streptavidin yielded high and prolonged liver accumulation (FIG. 17A) with an uptake level of 26%/g at 1 h increasing to 42–50%/g at 5–18 h and then decreasing 30%/g at 72 h (37%, 66–75% and 40%/whole liver, respectively). Lac-Av uptake was short term: 26%/g at 1 h followed by subsequent clearance (12%/g at 5 h and 2.3%/g at 18 h). No liver uptake of Lac-BSA (8.6:1) was observed at these time points, probably due to insufficient lactosylated BSA (BSA may require higher lactose derivatization for interaction with the ASGP receptor; Vera, 1984). Biodistribution of streptavidin alone at 5, 18 and 72 h in FIG. 17A shows high levels in the kidney (60–75%/g). The disposition characteristics of Lac-St showed rapid uptake by the liver, which is typical of carbohydrate-mediated parenchymal uptake and is different from the slow and gradual accumulation of TNP-St. It is also characterized by rapid elimination from blood and other tissues, except for liver, as was demonstrated for other Lac-macromolecules. This profile is different from that of St or TNP-St, where clearance of St or TNP-St from the non-target tissues is slower (see FIG. 17B: 0–60%/g; FIG. 17C: the same but at 0–10/g, range): At the 5 h time point, non-renal tissue levels of St was in the range of 3–8%/g and non-hepatic levels of TNP-St is in the range of 1–7%/g and 18%/g in blood. Non-hepatic values for Lac-St were 10–20 fold lower (0.1–0.36%/g). Targeting streptavidin to liver parenchymal cells can thus be effected by introducing lactose residues as a hepatotropic homing device.

EXAMPLE 16

Targeting Streptavidin to (RES) Via Antigen-Antibody Complexes

Figure 18A:
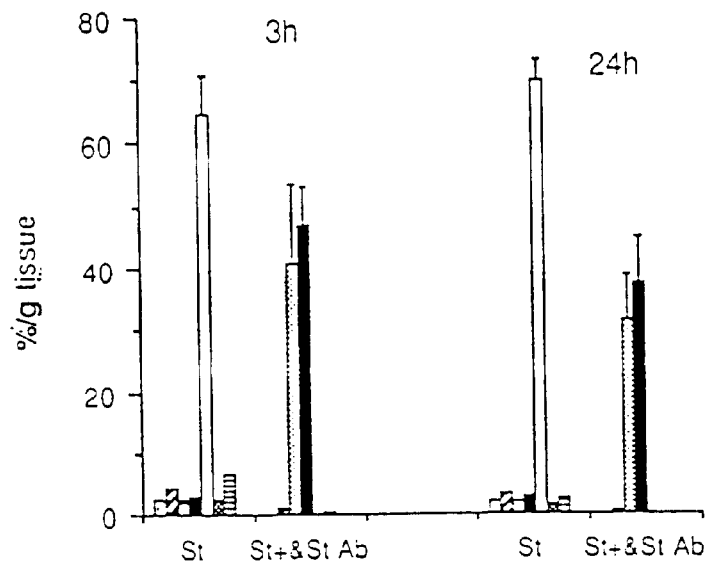
FIGS. 18A and 18B show the biodistribution of radioiodinated St and its complex with anti-streptavidin antibody (&St Ab.
Figure 18B:
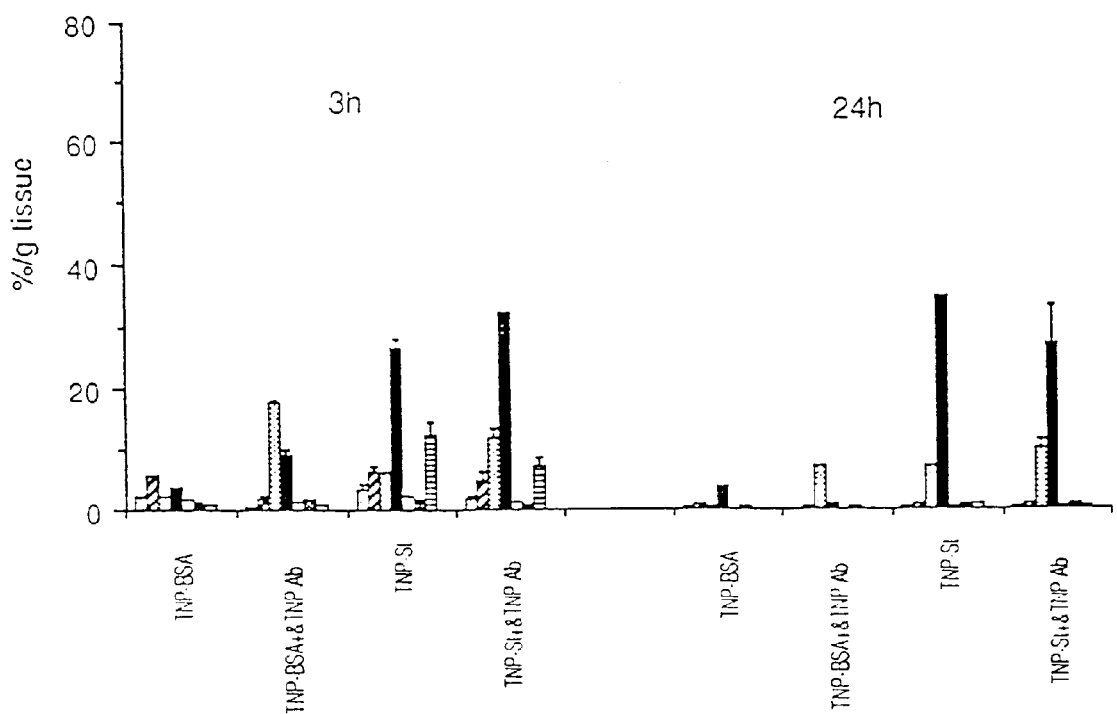

The in vivo biodistribution of streptavidin alone is characterized by normal clearance from blood and organs with the exception of the kidney where 70–80% of streptavidin is accumulated. Complexing $^{125}$I-streptavidin (St) to anti-streptavidin antibody (St Ab) modified its biodistribution pattern (FIG. 18A): high and prolonged levels of the complexed $^{125}$1I-streptavidin were found in both spleen and liver (42–44%/g at 3 h and 33–36%/g at 24 h) indicating the involvement of the spleen and liver RES in the uptake of antigen-antibody complexes via Fc-receptors on macrophages. A complex between TNP-BSA and anti-TNP antibody was cleared away as expected for a normally-degraded protein: 17%/g in the spleen and 9%/g in liver at 3 h which declined at 24 h to 7%/g in spleen and <1%/g in liver (FIG. 18B). The effect of anti-TNP antibody on TNP-St was less profound since TNP-St itself accumulates in the liver and, to a certain degree, also in the spleen. Liver level of TNP-St alone were as high as that of the St anti-St complex but spleen uptake was low (7–10%/g). This may indicate a vectorial transport of TNP-St to a restricted subpopulation of spleen macrophages. A complex between $^{125}$I-TNP-St and anti-TNP antibody had a pattern of biodistribution similar to that of $^{125}$I-TNP-St alone, except for some increase in spleen levels in the former (but not as high as for an antigen-antibody complex)

Enzyme resistant macromolecules, such as streptavidin or dextran, in their unmodified form or as TNP truncated derivatives, may thus serve as target vehicles to the RES. Targeting to the RES might be of importance in Gaucher disease, a lysosomal storage genetic disorder caused by a defect in the lysosomal enzyme glucocerebrosidase and consequent accumulation of glucocerebrosidase in the cells of the RES (Barranger et al., 1984). Clinical manifestations range from asymptomatic patients to severely affected infants through symptoms of anemia, bone damage, enlarged livers and spleens, severe central nervous system damage and death. Enzyme replacement therapy (with human mannose-terminated placental enzyme-alglucerase) has successfully reversed many of the manifestations of Gaucher disease but the high annual cost of treatment demonstrate the need for other alternatives including modifying enzyme distribution and stability (Martin BM et al., 1992) or targeted gene therapy (Ohashi et al., 1992).

TNP modification of streptavidin and avidin is shown in the examples to lead to 40–60% accumulation in total liver for a prolonged duration of several days. As demonstrated by immunohistochemistry, TNP-St is specifically localized in liver Kupffer cells which are part of the reticuloendothial system (RES) and represent 80–90% of all resident macrophages in the body. Lower specific accumulation is also observed in spleen macrophages. These two TNP-proteins are shown to target high and longterm doses of covalently bound radionuclide ($^{125}$I), low MW biotinylated ligands, such as biotinyl-tyrosine (BT) or a high MW biotinylated carrier, such as carboxymethyl dextran (CMdex, 40 kDa). Specific and prolonged liver targeting of chemotherapeutic agents (5-fluorouridine and cis-platin) bound or complexed to CMdex is also demonstrated. Chemical modification of streptavidin by lactosylation results in high and prolonged accumulation in liver hepatocytes. Thus, native or modified avidins can serve as tissue-selective vehicles for covalently linked ligands or for biotinylated carriers loaded with therapeutic or diagnostic agents, genes or other effector molecules.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aboud-Pirak et al., Proc. Natl. Acad. Sci. USA 68:3778–81 (1989)
Adzamil et al., Inves. Radiol. 26(2):143–8 (1991)
Arap et al., Science 279:377–380 (1998)
Argarana et al., Nucleic Acid Res. 14:1871–1882 (1986)
Arnon et al., "Horizons in Biochemistry and Biophysics" in Drug Carrier Systems Roerdin et al., Eds., John Wiley & Sons Ltd, 9:33–56 (1989)
Ashwell et al., Ann. Rev. Biochem. 51:5312–5544 (1982)
Barranger et al., in: The Molecular Basis of Lysosomal Storage Disorders, Barranger et al., Eds., New York: Academic Press, pp. 1677–1689 (1984)
Bayer et al., Biochem. J. 259:369–376 (1989)
Bayer et al., App. Biochem. Biotech. 53:1–9 (1995)
Bevilacqua et al., Science 243:1160–1165 (1989)
Brooks et al., Cell 79:1157–1164 (1994)
Cepek et al, Nature 372:190–193 (1994)
Chaiet et al., Archives of Biochemistry and Biophysics 106:1–5 (1964)
Chandra et al., Meth. Enzymol. 184:70–79 (1990)
Civitico et al., J. Med. Virol. 31:90–97 (1990)
Crance et al., J. Med. Viral. 31:155–160 (1990)
Di Bisceglie et al., Hepatology 16:649–654 (1992)
Di Bisceglie et al., Gastroenterology 105:858–862 (1993)
Duncan et al., S.T.P. Pharma Science 6:237–263 (1996)
Dunn et al. (Eds), Polymeric Drugs and Drug Delivery System ACS Symposium Series 469, American Chemical Society (Washington D.C., 1991)
Ellison et al., Protein Science 4:1337–1345 (1995)
Erbacher et al., Bioconjugate Chem. 6:401–410 (1995)
Folkman, J., Sci. Am. 275:116–119 (1996)
Fujita et al., J. Pharmacobio-Dyn. 14:623–629 (1991)
Fujita et al., J. Drug Targeting 2:157–165 (1994)
Gray, Arch. Biochem. Biophys. 163:426–428 (1974)
Green N. M., Advances in Protein Chemistry, 29:85–133 (1975)
Hashida et al., J. Controlled Release 36:99–107 (1995)
Hiller et al., Biochem. J. 278:573–585 (1991)
Hnatowich et al., J. Nuclear Med. 28:1294–1302 (1987)
Hurwitz et al., J. Applied Biochem. 2:25–35 (1980)
Hurwitz et al., J. Medicinal Chem. 28:137–140 (1985)
Johnson et al., J. Cell Biol. 121:1423–1432 (1993)
Johnston et al., Cell 56:1033–1044 (1989)
Kakumu et al., Gastroenterology 105:507–512 (1993)
Kedar et al., J. Immunother Emphasis Tumor Immunol 16:47–59 (1994)
Kikutani et al., Cell 47:657–665 (1986)
Lasky et al., Cell 56:1045–1055 (1989)
Ledley F. D., Hepatoloqy 18:1263–1273 (1993)
Ledley et al, Pediatric Research 33:313 (1993)
Lee et al., In: Neoglycoconjugates: Preparation and Application, Lee et al, Eds., Academic Press (San Diego, 1994), pp. 23–50
Longman et al., Cancer Chemother. Pharmacol. 36:91–101 (1995)
Magnusson et. al., Biochem. J. 257:651–656 (1989)
Martin et al., Am. J. Hum. Genet. 51:A307 (1992)
Matsumura et al., Cancer Research 46:6387–6392 (1986)
Miron et al., J. Solid Phase Biochemistry 1:225–236 (1976)
Monsigny et al., Adv. Drug Deliv 14:1–24 (1994)
Mulligan R. C., Science 260:926–932 (1993)
Natsumeda et al., Biochem. Biophys. Res. Commun. 153:321–327 (1988)
Neurath et al., J. Molec. Recog. 8:304–316 (1995)
Ohashi et al., Proc. Natl. Acad. Sci. USA 89:11332–11336 (1992)
Ouzan et al., Gastroenterol Clin. Biol. 11:568–573 (1987)
Pasqualini et al., Nature 380:364–366 (1996)
Pimm et al., J. Drug Target. 1:125–133 (1993)

Pimm et al., *J. Drug Target.* 3:375–383 (1996)
Pokutta et al., *Eur. J. Biochem.* 223:1019–1026 (1994)
Schechter et al., *Cancer Biochem. Biophys.* 8:277–288 (1986a)
Schechter et al., *Cancer Biochem. Biophys.* 8:289–298 (1986b)
Schechter et al., *Int. J. Cancer* 39:409–413 (1987a)
Schechter et al., *Cancer Immunol. Immunother.* 25:225 (1987b)
Schechter et al., *J. Controlled Release* 10:75–87 (1989a)
Schechter et al., *Cancer Chemother. Pharmacol.* 24:161–166 (1989b)
Schechter et al., *Eur. J. Biochem.* 462:327–331 (1990)
Schechter et al., *Int. J. Cancer* 48:243–256 (1991)
Schechter et al., *Kidney Int.* 47:1327–1335 (1995)
Schechter et al., *J. Drug Target.* 4:171–179 (1996)
Schwartz A. L., *CRC Crit. Rev. Biochem.* 16:207–223 (1984)
Schwartz et al., *Archives Biochem. Biophys.* 181:542–549 (1977)
Smedsrod et al., *Biochem. J.* 266:313–327 (1990)
Stahl et al., *Trends Biochem. Sci.* 5:194–196 (1980)
Taylor et al., *J. Biol. Chem.* 267:1719–1726 (1992)
Varner et al., "Tumor angiogenesis and the role of vascular cell integrin alphavbeta3", *Important Adv. Oncol.*, p. 69–87 (1996)
Vera et al., *I. Nucl. Med.* 25:779–787 (1984)
Wadhwa et al., *Bioconjugate Chem.* 6:283–291 (1995)
Wilchek et al., *Immunology Today* 5:39–43 (1984)
Wilchek et al., *Analytical Biochemistry* 171:1–32 (1988)
Wilchek et al., *Trends. Biochem. Sci.* 14:408–412 (1989)
Wilson et al., *J. Biol. Chem.* 267:963–967 (1992)
Wu et al., *Adv. Drug Delivery Reviews* 12:159–167 (1993)

What is claimed is:

1. An isolated modified avidin-type molecule, comprising an avidin-type molecule modified with a 2,4,6-trinitrophenyl (TNP) group or a lactosyl group at ε-amino groups of lysine residues for targeting said avidin-type molecule to the liver.

2. The modified avidin-type molecule according to claim 1, wherein said avidin-type molecule is selected from the group consisting of native egg white avidin, recombinant avidin, deglycosylated forms of avidin, streptavidin, recombinant streptavidin, and derivatives thereof obtained from said avidin-type molecule by modifying at arginine residues.

3. The modified avidin-type molecule according to claim 1, wherein said avidin-type molecule is selected from the group consisting of streptavidin and recombinant streptavidin.

4. The modified avidin-type molecule according to claim 1, wherein said avidin-type molecule is radiolabeled.

5. The modified avidin-type molecule according to claim 4, wherein said avidin-type molecule is radiolabeled with a radionuclide selected from the group consisting of $^{111}$In, $^{125}$I, $^{131}$I and $^{99m}$Tc.

6. A composition for diagnosing hepatic disorders, comprising a pharmaceutically acceptable excipient and the modified avidin-type molecule of claim 4.

7. A pharmaceutical composition for treating hepatic disorders, comprising a pharmaceutically acceptable excipient and an effective amount of the modified avidin-type molecule of claim 4.

8. The modified avidin-type molecule according to claim 1, which is conjugated or complexed to a therapeutic agent for treating hepatic disorders.

9. The modified avidin-type molecule according to claim 8, wherein said therapeutic agent is a chemotherapeutic agent.

10. The modified avidin-type molecule according to claim 8, wherein said therapeutic agent is an antiviral drug.

11. A pharmaceutical composition for treating hepatic disorders, comprising a pharmaceutically acceptable excipient and an effective amount of the modified avidin-type molecule of claim 8.

12. The modified avidin-type molecule according to claim 1, which is conjugated or complexed to an agent for detection of targeted cells in the liver.

13. A composition for detecting hepatic disorders, comprising a pharmaceutically acceptable excipient and the modified avidin-type molecule of claim 12.

14. The modified avidin-type molecule according to claim 1, which is conjugated or complexed to a biotinylated therapeutic agent for treating hepatic disorders.

15. The modified avidin-type molecule according to claim 14, wherein said biotinylated therapeutic agent is a chemotherapeutic agent.

16. The modified avidin-type molecule according to claim 15, wherein said chemotherapeutic agent is doxorubicin.

17. The modified avidin-type molecule according to claim 15, wherein said chemotherapeutic agent is a mitomycin.

18. The modified avidin-type molecule according to claim 15, wherein said chemotherapeutic agent is cisplatin.

19. The modified avidin-type molecule according to claim 15, wherein said chemotherapeutic agent is fluorouracil.

20. The modified avidin-type molecule according to claim 15, wherein said chemotherapeutic agent is fluorouridine.

21. The modified avidin-type molecule according to claim 15, wherein said chemotherapeutic agent is tiazofurin.

22. The modified avidin-type molecule according to claim 14, wherein said biotinylated therapeutic agent is an antiviral drug.

23. The modified avidin-type molecule according to claim 22, wherein said antiviral drug is interferon-alpha.

24. The modified avidin-type molecule according to claim 22, wherein said antiviral drug is interferon-beta.

25. The modified avidin-type molecule according to claim 22, wherein said antiviral drug is ribavirin.

26. The modified avidin-type molecule according to claim 22, wherein said antiviral drug is vidarabine.

27. The modified avidin-type molecule according to claim 14, wherein said biotinylated therapeutic agent is further conjugated or complexed to a polymer or to a liposome.

28. The modified avidin-type molecule according to claim 27, wherein said biotinylated therapeutic agent is conjugated or complexed to a polymer.

29. A pharmaceutical composition for treating hepatic disorders, comprising a pharmaceutically acceptable excipient and an effective amount of the modified avidin-type molecule of claim 14.

30. The modified avidin-type molecule according to claim 1, which is conjugated or complexed to a biotinylated agent for detection of targeted cells in the liver.

31. The modified avidin-type molecule according to claim 30, wherein the biotinylated agent is a magnetic resonance imaging label selected from gadolinium complexes of the group consisting of diethylene triaminepentaacetic acid (Gd-DTPA) and phosphonate Gd-DTPA, and wherein the biotinylated agent is further conjugated or complexed to poly-L-lysin.

32. The modified avidin-type molecule according to claim 30, wherein said biotinylated agent is further conjugated or complexed to a polymer or to a liposome.

33. The modified avidin-type molecule according to claim 32, wherein a heavy metal is attached to said polymer.

34. The modified avidin-type molecule according to claim 33, wherein the heavy metal is selected from the group consisting of Pt, Au, and Tl.

35. A composition for detecting hepatic disorders, comprising a pharmaceutically acceptable excipient and the modified avidin-type molecule of claim 32.

36. A composition for detecting hepatic disorders, comprising a pharmaceutically acceptable excipient and the modified avidin-type molecule of claim 30.

37. The modified avidin-type molecule according to claim 30, wherein said biotinylated therapeutic agent is further conjugated or complexed to a polymer or to a liposome.

38. The modified avidin-type molecule according to claim 37, wherein said biotinylated therapeutic agent is conjugated or complexed to a polymer.

* * * * *